United States Patent [19]

Fahnestock

[11] Patent Number: 4,954,618
[45] Date of Patent: Sep. 4, 1990

[54] CLONED STREPTOCOCCAL GENES ENCODING PROTEIN G AND THEIR USE TO CONSTRUCT RECOMBINANT MICROORGANISMS TO PRODUCE PROTEIN G

[75] Inventor: Stephen R. Fahnestock, Olney, Md.

[73] Assignee: Genex Corporation, Gaithersburg, Md.

[21] Appl. No.: 280,963

[22] Filed: Mar. 15, 1989

Related U.S. Application Data

[60] Division of Ser. No. 63,959, Jun. 1987, which is a continuation-in-part of PCT US87/00329 filed Feb. 17, 1987, which is a continuation-in-part of Ser. No. 854,887, Apr. 23, 1986, abandoned, which is a continuation-in-part of Ser. No. 829,354, Feb. 14, 1986, abandoned.

[51] Int. Cl.$^5$ .................... C07K 3/00; C08H 1/00; C12N 15/00
[52] U.S. Cl. ................. 530/387; 435/172.3; 530/413; 530/415; 530/811; 935/11
[58] Field of Search ............... 530/387, 415, 811; 570/413

[56] References Cited

FOREIGN PATENT DOCUMENTS

| | | |
|---|---|---|
| 0127328 | 12/1984 | European Pat. Off. |
| 0131142 | 1/1985 | European Pat. Off. |
| 0200909 | 12/1986 | European Pat. Off. |
| 0284368 | 9/1988 | European Pat. Off. |
| WO87/5025 | 8/1987 | PCT Int'l Appl. |
| WO87/5631 | 9/1987 | PCT Int'l Appl. |

OTHER PUBLICATIONS

Guss, B. et al., *Embo J.* 5:1567–1575 (1986).
Akerstrom, B. et al., *J. Biol. Chem.* 261:10240–10247 (1986).
Reis, K. J. et al., *J. Immunol.* 132:3098–3102 (1984).
Akerstrom, B. et al., *J. Immunol.* 135:2589–2592 (1985).
Von Mering, G. O. et al., *Mol. Immunol.* 23:811–812 (1986).
Bjorck, L. et al., *J. Immunol.* 133:969–974 (1984).
Reis, K. J. et al., *J. Immunol.* 132:3091–3097 (1984).
Boyle, M. D. P., *BioTechniques* 334–340 (1984).
Reis, K. J. et al., *Mol. Immunol.* 23:425–431 (1986).
Myhre, E. B. et al., *Infect. Immun.* 17:475–482 (1977).
Kronvall, G. et al., *J. Immunol.* 111:1401–1406 (1973).
Myhre, E. B. et al., *Infect Immun.* 23:1–7 (1979).
Young, M. in *Genetics and Biotechnology of Bacilli*, Ganesan et al. (eds.), pp. 89–103, Academic Press, Orlando (1984).
Yoneda, Y. et al., *Biochem. Biophys. Res. Commun.* 91:1556–1564 (1979).
Hofemeister et al., *Mol. Gen. Genet.* 189:58–68 (1983).
Grinter, N. J., *Gene* 21:133–143 (1983).
Yamaguchi, K. et al., *Mol. Gen. Genet.* 178:525–533 (1980).
Harding, N. E. et al., *J. Bacter.* 152:983–993 (1982).

*Primary Examiner*—Thomas D. Mays
*Attorney, Agent, or Firm*—Saidman, Sterne, Kessler & Goldstein

[57] ABSTRACT

A cloned gene encoding Protein G, or functionally active portions thereof, vectors containing the cloned gene, and microorganisms transformed by those vectors are disclosed.

6 Claims, 16 Drawing Sheets

PARTIAL RESTRICTION MAP OF PLASMID pGX4533

```
AAGCTTTGGTGGAGAAATTGGCTGGCGAATCCAGCTTCACCGGTGTTTCA       50

CCAGTAGATGCTTTCTGTGGTCTTATTGACACGCACTTGTGGCGAGAGTA      100

CTAACAGTCACAGCGACGTTAACTTTATTTTCCTTATGAGAGGTTAAGAA      150

AAAACGTTATTAAATAGCAGAAAAGAATATTATGACTGACGTTAGGAGTT      200

TTCTCCTAACGTTTTTTTAGTACAAAAAGAGAATTCTCTATTATAAATA       250

AAATAAATAGTACTATAGATAGAAATCTCATTTTTAAAAAGTCTTGTTT       300

TCTTAAAGAAGAAAATAATTGTTGAAAAATTATAGAAAATCATTTTTATA      350

CTAATGAAATAGACATAAGGCTAAATTGGTGAGGTGATGATAGGAGATTT      400

ATTTGTAAGGATTCCTTAATTTTATTAATTCAACAAAAATTGATAGAAAA      450

ATTAAATGGAATCCTTGATTTAATTTTATTAAGTTGTATAATAAAAAGTG      500
                   ‾‾‾‾‾                ‾‾‾‾‾‾
                    -35                   -10
```

```
AAATTATTAAATCGTAGTTTCAAATTTGTCGGCTTTTTAATATGTGCTGG      550
```

```
                                    MET GLU LYS GLU LYS
CATATTAAAATTAAAAAAGGAGAAAAA         ATG GAA AAA GAA AAA    592
                  ‾‾‾‾‾‾
                   rbs
```

```
                         10
LYS VAL LYS TYR PHE LEU ARG LYS SER ALA PHE GLY LEU
AAG GTA AAA TAC TTT TTA CGT AAA TCA GCT TTT GGG TTA       631

20                                       30
ALA SER VAL SER ALA ALA PHE LEU VAL GLY SER THR VAL
GCA TCC GTA TCA GCT GCA TTT TTA GTG GGA TCA ACG GTA       670

40
PHE ALA VAL ASP SER PRO ILE GLU ASP THR PRO ILE ILE
TTC GCT GTT GAT TCA CCA ATC GAA GAT ACC CCA ATT ATT       709

50
ARG ASN GLY GLY GLU LEU THR ASN LEU LEU GLY ASN SER
CGT AAT GGT GGT GAA TTA ACT AAT CTT CTG GGG AAT TCA       748

60                                       70
GLU THR THR LEU ALA LEU ARG ASN GLU GLU SER ALA THR
GAG ACA ACA CTG GCT TTG CGT AAT GAA GAG AGT GCT ACA       787
```

FIG. 3

| | | | | | | | | | 80 | | | | |
|---|---|---|---|---|---|---|---|---|---|---|---|---|---|
| ALA | ASP | LEU | THR | ALA | ALA | ALA | VAL | ALA | ASP | THR | VAL | ALA | |
| GCT | GAT | TTG | ACA | GCA | GCA | GCG | GTA | GCC | GAT | ACT | GTG | GCA | 826 |
| ALA | ALA | ALA | ALA | GLU | ASN | 90 ALA | GLY | ALA | ALA | ALA | TRP | GLU | |
| GCA | GCG | GCA | GCT | GAA | AAT | GCT | GGG | GCA | GCA | GCT | TGG | GAA | 865 |
| ALA | ALA | ALA | 100 ALA | ALA | ASP | ALA | LEU | ALA | LYS | ALA | LYS | ALA | |
| GCA | GCG | GCA | GCA | GCA | GAT | GCT | CTA | GCA | AAA | GCC | AAA | GCA | 904 |
| 110 ASP | ALA | LEU | LYS | GLU | PHE | ASN | LYS | TYR | GLY | 120 VAL | SER | ASP | |
| GAT | GCC | CTT | AAA | GAA | TTC | AAC | AAA | TAT | GGA | GTA | AGT | GAC | 943 |
| TYR | TYR | LYS | ASN | LEU | ILE | ASN | 130 ASN | ALA | LYS | THR | VAL | GLU | |
| TAT | TAC | AAG | AAT | CTA | ATC | AAC | AAT | GCC | AAA | ACT | GTT | GAA | 982 |
| GLY | ILE | LYS | ASP | 140 LEU | GLN | ALA | GLN | VAL | VAL | GLU | SER | ALA | |
| GGC | ATA | AAA | GAC | CTT | CAA | GCA | CAA | GTT | GTT | GAA | TCA | GCG | 1021 |
| LYS | 150 LYS | ALA | ARG | ILE | SER | GLU | ALA | THR | ASP | GLY | 160 LEU | SER | |
| AAG | AAA | GCG | CGT | ATT | TCA | GAA | GCA | ACA | GAT | GGC | TTA | TCT | 1060 |
| ASP | PHE | LEU | LYS | SER | GLN | THR | 170 PRO | ALA | GLU | ASP | THR | VAL | |
| GAT | TTC | TTG | AAA | TCG | CAA | ACA | CCT | GCT | GAA | GAT | ACT | GTT | 1099 |
| LYS | SER | ILE | GLU | LEU | 180 ALA | GLU | ALA | LYS | VAL | LEU | ALA | ASN | |
| AAA | TCA | ATT | GAA | TTA | GCT | GAA | GCT | AAA | GTC | TTA | GCT | AAC | 1138 |
| ARG | GLU | 190 LEU | ASP | LYS | TYR | GLY | VAL | SER | ASP | TYR | HIS | 200 LYS | |
| AGA | GAA | CTT | GAC | AAA | TAT | GGA | GTA | AGT | GAC | TAT | CAC | AAG | 1177 |
| ASN | LEU | ILE | ASN | ASN | ALA | LYS | THR | VAL | 210 GLU | GLY | VAL | LYS | |
| AAC | CTA | ATC | AAC | AAT | GCC | AAA | ACT | GTT | GAA | GGT | GTA | AAA | 1216 |
| GLU | LEU | ILE | ASP | GLU | ILE | 220 LEU | ALA | ALA | LEU | PRO | LYS | THR | |
| GAA | CTG | ATA | GAT | GAA | ATT | TTA | GCT | GCA | TTA | CCT | AAG | ACT | 1255 |
| ASP | THR | TYR | 230 LYS | LEU | ILE | LEU | ASN | GLY | LYS | THR | LEU | LYS | |
| GAC | ACT | TAC | AAA | TTA | ATC | CTT | AAT | GGT | AAA | ACA | TTG | AAA | 1294 |

FIG. 3A

| | | | | | | | | | | | | | | |
|---|---|---|---|---|---|---|---|---|---|---|---|---|---|---|
| 240 GLY GGC | GLU GAA | THR ACA | THR ACT | THR ACT | GLU GAA | ALA GCT | VAL GTT | ASP GAT | ALA GCT | 250 ALA GCT | THR ACT | ALA GCA | | 1333 |
| GLU GAA | LYS AAA | VAL GTC | PHE TTC | LYS AAA | GLN CAA | TYR TAC | 260 ALA GCT | ASN AAC | ASP GAC | ASN AAC | GLY GGT | VAL GTT | | 1372 |
| ASP GAC | GLY GGT | GLU GAA | TRP TGG | 270 THR ACT | TYR TAC | ASP GAC | ASP GAT | ALA GCG | THR ACT | LYS AAG | THR ACC | PHE TTT | | 1411 |
| THR ACA | 280 VAL GTT | THR ACT | GLU GAA | LYS AAA | PRO CCA | GLU GAA | VAL GTG | ILE ATC | ASP GAT | ALA GCG | 290 SER TCT | GLU GAA | | 1450 |
| LEU TTA | THR ACA | PRO CCA | ALA GCC | VAL GTG | THR ACA | THR ACT | TYR TAC | 300 LYS AAA | LEU CTT | VAL GTT | ILE ATT | ASN AAT | | 1489 |
| GLY GGT | LYS AAA | THR ACA | LEU TTG | LYS AAA | 310 GLY GGC | GLU GAA | THR ACA | THR ACT | THR ACT | LYS AAA | ALA GCA | VAL GTA | | 1528 |
| ASP GAC | ALA GCA | 320 GLU GAA | THR ACT | ALA GCA | GLU GAA | LYS AAA | ALA GCC | PHE TTC | LYS AAA | GLN CAA | TYR TAC | 330 ALA GCT | | 1567 |
| ASN AAC | ASP GAC | ASN AAC | GLY GGT | VAL GTT | ASP GAT | GLY GGT | VAL GTT | TRP TGG | 340 THR ACT | TYR TAT | ASP GAT | ASP GAT | | 1606 |
| ALA GCG | THR ACT | LYS AAG | THR ACC | PHE TTT | THR ACG | 350 VAL GTA | THR ACT | GLU GAA | MET ATG | VAL GTT | THR ACA | GLU GAG | | 1645 |
| VAL GTT | PRO CCT | GLY GGT | 360 ASP GAT | ALA GCA | PRO CCA | THR ACT | GLU GAA | PRO CCA | GLU GAA | LYS AAA | PRO CCA | GLU GAA | | 1684 |
| 370 ALA GCA | SER AGT | ILE ATC | PRO CCT | LEU CTT | VAL GTT | PRO CCG | LEU TTA | THR ACT | PRO CCT | 380 ALA GCA | THR ACT | PRO CCA | | 1723 |
| ILE ATT | ALA GCT | LYS AAA | ASP GAT | ASP GAC | ALA GCT | LYS AAG | 390 LYS AAA | ASP GAC | ASP GAT | THR ACT | LYS AAG | LYS AAA | | 1762 |
| GLU GAA | ASP GAT | ALA GCT | LYS AAA | 400 LYS AAA | PRO CCA | GLU GAA | ALA GCT | LYS AAG | LYS AAA | ASP GAT | ASP GAC | ALA GCT | | 1801 |

FIG. 3B

```
        410                                                    420
LYS     LYS     ALA     GLU     THR     LEU     PRO     THR     THR     GLY     GLU     GLY     SER
AAG     AAA     GCT     GAA     ACT     CTT     CCT     ACA     ACT     GGT     GAA     GGA     AGC     1840

430
ASN     PRO     PHE     PHE     THR     ALA     ALA     ALA     LEU     ALA     VAL     MET     ALA
AAC     CCA     TTC     TTC     ACA     GCA     GCT     GCG     CTT     GCA     GTA     ATG     GCT     1879

440
GLY     ALA     GLY     ALA     LEU     ALA     VAL     ALA     SER     LYS     ARG     LYS     GLU
GGT     GCG     GGT     GCT     TTG     GCG     GTC     GCT     TCA     AAA     CGT     AAA     GAA     1918

ASP     ***
GAC     TAATTGTCATTATTTTTGACAAAAAGCTT  1950
```

FIG. 3C

```
        410                                                    420
LYS     LYS     ALA     GLU     THR     LEU     PRO     THR     THR     GLY     GLU     GLY     SER
AAG     AAA     GCT     GAA     ACT     CTT     CCT     ACA     ACT     GGT     GAA     GGA     AGC     1840

430
ASN     PRO     PHE     PHE     THR     ALA     ALA     ALA     LEU     ALA     VAL     MET     ALA
AAC     CCA     TTC     TTC     ACA     GCA     GCT     GCG     CTT     GCA     GTA     ATG     GCT     1879

440
GLY     ALA     GLY     ALA     LEU     ALA     VAL     ALA     SER     LYS     ARG     LYS     GLU
GGT     GCG     GGT     GCT     TTG     GCG     GTC     GCT     TCA     AAA     CGT     AAA     GAA     1918

ASP     ***
GAC     TAATTGTCATTATTTTTGACAAAAAGCTT  1950
```

FIG. 8C

RESTRICTION MAP OF THE CLONED PROTEIN G GENE AND THE REPEATING STRUCTURE OF ITS PROTEIN PRODUCT

```
AAGCTTTGGTGGAGAAATTGGCTGGCGAATCCAGCTTCACCGGTGTTTCA      50

CCAGTAGATGCTTTCTGTGGTCTTATTGACACGCACTTGTGGCGAGAGTA     100

CTAACAGTCACAGCGACGTTAACTTTATTTTCCTTATGAGAGGTTAAGAA     150

AAAACGTTATTAAATAGCAGAAAAGAATATTATGACTGACGTTAGGAGTT     200

TTCTCCTAACGTTTTTTTAGTACAAAAAGAGAATTCTCTATTATAAATA     250

AAATAAATAGTACTATAGATAGAAAATCTCATTTTTAAAAAGTCTTGTTT     300

TCTTAAAGAAGAAAATAATTGTTGAAAAATTATAGAAAATCATTTTTATA     350

CTAATGAAATAGACATAAGGCTAAATTGGTGAGGTGATGATAGGAGATTT     400

ATTTGTAAGGATTCCTTAATTTTATTAATTCAACAAAAATTGATAGAAAA     450

ATTAAATGGAATCCTTGATTTAATTTTATTAAGTTGTATAATAAAAAGTG     500
                   ‾‾‾‾‾                 ‾‾‾‾‾‾
                    -35                    -10

AAATTATTAAATCGTAGTTTCAAATTTGTCGGCTTTTTAATATGTGCTGG     550
```

|   |   |   |   |   |   |   |   |   | MET | GLU | LYS | GLU | LYS |   |
|---|---|---|---|---|---|---|---|---|---|---|---|---|---|---|
| CATATTAAAATTAAA<u>AAAGGAG</u>AAAAA | | | | | | | | | ATG | GAA | AAA | GAA | AAA | 592 |
|   |   |   | rbs |   |   |   |   |   |   |   |   |   |   |   |

|   |   |   |   | 10 |   |   |   |   |   |   | 30 |   |
|---|---|---|---|---|---|---|---|---|---|---|---|---|
| LYS | VAL | LYS | TYR | PHE | LEU | ARG | LYS | SER | ALA | PHE | GLY | LEU |
| AAG | GTA | AAA | TAC | TTT | TTA | CGT | AAA | TCA | GCT | TTT | GGG | TTA | 631 |

|   | 20 |   |   |   |   |   |   |   |   | 30 |   |
|---|---|---|---|---|---|---|---|---|---|---|---|
| ALA | SER | VAL | SER | ALA | ALA | PHE | LEU | VAL | GLY | SER | THR | VAL |
| GCA | TCC | GTA | TCA | GCT | GCA | TTT | TTA | GTG | GGA | TCA | ACG | GTA | 670 |

|   |   |   |   |   |   |   | 40 |   |   |   |   |
|---|---|---|---|---|---|---|---|---|---|---|---|
| PHE | ALA | VAL | ASP | SER | PRO | ILE | GLU | ASP | THR | PRO | ILE | ILE |
| TTC | GCT | GTT | GAT | TCA | CCA | ATC | GAA | GAT | ACC | CCA | ATT | ATT | 709 |

|   |   |   |   | 50 |   |   |   |   |   |   |   |
|---|---|---|---|---|---|---|---|---|---|---|---|
| ARG | ASN | GLY | GLY | GLU | LEU | THR | ASN | LEU | LEU | GLY | ASN | SER |
| CGT | AAT | GGT | GGT | GAA | TTA | ACT | AAT | CTT | CTG | GGG | AAT | TCA | 748 |

|   |   | 60 |   |   |   |   |   |   |   |   | 70 |   |
|---|---|---|---|---|---|---|---|---|---|---|---|---|
| GLU | THR | THR | LEU | ALA | LEU | ARG | ASN | GLU | GLU | SER | ALA | THR |
| GAG | ACA | ACA | CTG | GCT | TTG | CGT | AAT | GAA | GAG | AGT | GCT | ACA | 787 |

FIG. 8

| | | | | | | | | | 80 | | | | |
|---|---|---|---|---|---|---|---|---|---|---|---|---|---|
| ALA | ASP | LEU | THR | ALA | ALA | ALA | VAL | ALA | ASP | THR | VAL | ALA | |
| GCT | GAT | TTG | ACA | GCA | GCA | GCG | GTA | GCC | GAT | ACT | GTG | GCA | 826 |
| ALA | ALA | ALA | ALA | GLU | ASN | 90 ALA | GLY | ALA | ALA | ALA | TRP | GLU | |
| GCA | GCG | GCA | GCT | GAA | AAT | GCT | GGG | GCA | GCA | GCT | TGG | GAA | 865 |
| ALA | ALA | ALA | 100 ALA | ALA | ASP | ALA | LEU | ALA | LYS | ALA | LYS | ALA | |
| GCA | GCG | GCA | GCA | GCA | GAT | GCT | CTA | GCA | AAA | GCC | AAA | GCA | 904 |
| 110 ASP | ALA | LEU | LYS | GLU | PHE | ASN | LYS | TYR | GLY | 120 VAL | SER | ASP | |
| GAT | GCC | CTT | AAA | GAA | TTC | AAC | AAA | TAT | GGA | GTA | AGT | GAC | 943 |
| TYR | TYR | LYS | ASN | LEU | ILE | ASN | 130 ASN | ALA | LYS | THR | VAL | GLU | |
| TAT | TAC | AAG | AAT | CTA | ATC | AAC | AAT | GCC | AAA | ACT | GTT | GAA | 982 |
| GLY | ILE | LYS | ASP | 140 LEU | GLN | ALA | GLN | VAL | VAL | GLU | SER | ALA | |
| GGC | ATA | AAA | GAC | CTT | CAA | GCA | CAA | GTT | GTT | GAA | TCA | GCG | 1021 |
| LYS | 150 LYS | ALA | ARG | ILE | SER | GLU | ALA | THR | ASP | GLY | 160 LEU | SER | |
| AAG | AAA | GCG | CGT | ATT | TCA | GAA | GCA | ACA | GAT | GGC | TTA | TCT | 1060 |
| ASP | PHE | LEU | LYS | SER | GLN | THR | 170 PRO ALA | GLU | ASP | THR | VAL | | |
| GAT | TTC | TTG | AAA | TCG | CAA | ACA | CCT | GCT | GAA | GAT | ACT | GTT | 1099 |
| LYS | SER | ILE | GLU | LEU | 180 ALA | GLU | ALA | LYS | VAL | LEU | ALA | ASN | |
| AAA | TCA | ATT | GAA | TTA | GCT | GAA | GCT | AAA | GTC | TTA | GCT | AAC | 1138 |
| ARG | GLU | 190 LEU | ASP | LYS | TYR | GLY | VAL | SER | ASP | TYR | HIS | 200 LYS | |
| AGA | GAA | CTT | GAC | AAA | TAT | GGA | GTA | AGT | GAC | TAT | CAC | AAG | 1177 |
| ASN | LEU | ILE | ASN | ASN | ALA | LYS | THR | VAL | 210 GLU | GLY | VAL | LYS | |
| AAC | CTA | ATC | AAC | AAT | GCC | AAA | ACT | GTT | GAA | GGT | GTA | AAA | 1216 |
| GLU | LEU | ILE | ASP | GLU | ILE | 220 LEU | ALA | ALA | LEU | PRO | LYS | THR | |
| GAA | CTG | ATA | GAT | GAA | ATT | TTA | GCT | GCA | TTA | CCT | AAG | ACT | 1255 |
| ASP | THR | TYR | 230 LYS | LEU | ILE | LEU | ASN | GLY | LYS | THR | LEU | LYS | |
| GAC | ACT | TAC | AAA | TTA | ATC | CTT | AAT | GGT | AAA | ACA | TTG | AAA | 1294 |

| 240 | | | | | | | | | 250 | | | | |
|---|---|---|---|---|---|---|---|---|---|---|---|---|---|
| GLY | GLU | THR | THR | THR | GLU | ALA | VAL | ASP | ALA | ALA | THR | ALA | |
| GGC | GAA | ACA | ACT | ACT | GAA | GCT | GTT | GAT | GCT | GCT | ACT | GCA | 1333 |

B1

| | | | | | | | 260 | | | | | | |
|---|---|---|---|---|---|---|---|---|---|---|---|---|---|
| GLU | LYS | VAL | PHE | LYS | GLN | TYR | ALA | ASN | ASP | ASN | GLY | VAL | |
| GAA | AAA | GTC | TTC | AAA | CAA | TAC | GCT | AAC | GAC | AAC | GGT | GTT | 1372 |

B1

| | | | 270 | | | | | | | | | | |
|---|---|---|---|---|---|---|---|---|---|---|---|---|---|
| ASP | GLY | GLU | TRP | THR | TYR | ASP | ASP | ALA | THR | LYS | THR | PHE | |
| GAC | GGT | GAA | TGG | ACT | TAC | GAC | GAT | GCG | ACT | AAG | ACC | TTT | 1411 |

B1

| 280 | | | | | | | | | 290 | | | | |
|---|---|---|---|---|---|---|---|---|---|---|---|---|---|
| THR | VAL | THR | GLU | LYS | PRO | GLU | VAL | ILE | ASP | ALA | SER | GLU | |
| ACA | GTT | ACT | GAA | AAA | CCA | GAA | GTG | ATC | GAT | GCG | TCT | GAA | 1450 |

B1  b

| | | | | | | | 300 | | | | | |
|---|---|---|---|---|---|---|---|---|---|---|---|---|
| LEU | THR | PRO | ALA | VAL | THR | THR | TYR | LYS | LEU | VAL | ILE | ASN |
| TTA | ACA | CCA | GCC | GTG | ACA | ACT | TAC | AAA | CTT | GTT | ATT | AAT | 1489 | b  B2

| | | | | 310 | | | | | | | |
|---|---|---|---|---|---|---|---|---|---|---|---|
| GLY | LYS | THR | LEU | LYS | GLY | GLU | THR | THR | THR | LYS | ALA | VAL |
| GGT | AAA | ACA | TTG | AAA | GGC | GAA | ACA | ACT | ACT | AAA | GCA | GTA | 1528 |

B2

| | | 320 | | | | | | | | | | 330 | |
|---|---|---|---|---|---|---|---|---|---|---|---|---|---|
| ASP | ALA | GLU | THR | ALA | GLU | LYS | ALA | PHE | LYS | GLN | TYR | ALA | |
| GAC | GCA | GAA | ACT | GCA | GAA | AAA | GCC | TTC | AAA | CAA | TAC | GCT | 1567 |

B2

| | | | | | | | 340 | | | | |
|---|---|---|---|---|---|---|---|---|---|---|---|
| ASN | ASP | ASN | GLY | VAL | ASP | GLY | VAL | TRP | THR | TYR | ASP | ASP |
| AAC | GAC | AAC | GGT | GTT | GAT | GGT | GTT | TGG | ACT | TAT | GAT | GAT | 1606 |

B2

| | | | | | 350 | | | | | | |
|---|---|---|---|---|---|---|---|---|---|---|---|
| ALA | THR | LYS | THR | PHE | THR | VAL | THR | GLU | MET | VAL | THR | GLU |
| GCG | ACT | AAG | ACC | TTT | ACG | GTA | ACT | GAA | ATG | GTT | ACA | GAG | 1645 |

B2

| | | 360 | | | | | | | | | |
|---|---|---|---|---|---|---|---|---|---|---|---|
| VAL | PRO | GLY | ASP | ALA | PRO | THR | GLU | PRO | GLU | LYS | PRO | GLU |
| GTT | CCT | GGT | GAT | GCA | CCA | ACT | GAA | CCA | GAA | AAA | CCA | GAA | 1684 |

| 370 | | | | | | | | | 380 | | | |
|---|---|---|---|---|---|---|---|---|---|---|---|---|
| ALA | SER | ILE | PRO | LEU | VAL | PRO | LEU | THR | PRO | ALA | THR | PRO |
| GCA | AGT | ATC | CCT | CTT | GTT | CCG | TTA | ACT | CCT | GCA | ACT | CCA | 1723 |

| | | | | | 390 | | | | | |
|---|---|---|---|---|---|---|---|---|---|---|
| ILE | ALA | LYS | ASP | ASP | ALA | LYS | LYS | ASP | ASP | THR | LYS | LYS |
| ATT | GCT | AAA | GAT | GAC | GCT | AAG | AAA | GAC | GAT | ACT | AAG | AAA | 1762 |

| | | | 400 | | | | | | | | |
|---|---|---|---|---|---|---|---|---|---|---|---|
| GLU | ASP | ALA | LYS | LYS | PRO | GLU | ALA | LYS | LYS | ASP | ASP | ALA |
| GAA | GAT | GCT | AAA | AAA | CCA | GAA | GCT | AAG | AAA | GAT | GAC | GCT | 1801 |

FIG. 8B

The DNA and Amino Acid Sequences for the Protein G Gene
Derived from Streptococcus GX 7805

```
                                                                                                                              121
AGCTTTGGTGGAGAAATTGGCTGGCGAATCCAACTTCACCGGTGTTTCTGTGCCTTCTGTGCCGAGAGTACTAACAGTCACACGACGTTA

241
ACCTTATTTTCCTTATGAGAGGTTAAGAAAAACCCTTATTAAATGACTAGCAGAAAGAATATATGACTGACGTTAGGAGTTTTCTCCCTAACGTTTTTTTAGTACAAAAGAGAATTCTCTA

361
TTATAAATAAAATAAATAGTACTATAGATAGAAATCTCATTTTTAAAAGTCTTGTTTTCTTAAAGAAGAAATAATTGTTGAAAAATTATAGAAAATCATTTTTATACTAATGAAATA

481
GACATAAGGCTAAATTGGTGAGGTTATGATAGGAGATTTATTTGTAAGGATTCCTTAATTTTATTAATTCAACAAAAATTGATAGAAAAATTAATGAAATCCTTGATTTAATTTTATTA
                                                                -35
                                                                                           rbs       Met Glu Lys Glu Lys Val Lys    601
AGTTGTATAATAAAGTGAAATTATTAATCGTAGTTTCAAATTTGTCGCTTTTAATATGTCTGCCATATTAAAATTAAAAAGGAGAAAAATGGAAAAAGAAAAAGTAAAA
  -10                                                                                                                        
                         V
                                                                                                                              721
TyrPheLeuArgLysSerAlaAlaPheGlyLeuAlaSerValSerAlaAlaPheLeuValGlySerThrValPheAlaValAspSerProIleGluAspThrProIleIleArgAsnGlyGly
TACTTTTTACGTAAATCAGCTTTTGGTTTAGCATCCGTTAGCGCTGCATTTGTTGGATCAACCGTATTCGCTGTTGACTCAACTCCGAAGATACCCCAATTATTCGTAATGGTGGT GluLeuThrAsnLeuGlyAsnSerGluThrLeuAlaLeuArgAsnGlyAspLeuThrAlaAlaValAlaAlaAlaAlaAspThrValAlaAlaAlaAlaAlaGlu                    841
GAATTAACTAATCTTGGGGAATTCAGAGACAACACTGCTTTGCGTAATGACGAAGAGTGCTACAGCTGCTGTTGACAGCAGCAGTGCGGTGATCGCTGGCAGCGGCAGCTGAA AsnAlaGlyAlaAlaAlaTrpGluAlaAlaAlaAlaAlaAlaAspAlaAlaLeuAlaLysAlaAlaAspAlaLeuAlaLysGluPheAsnLysGluLysTyrGlyValSerAspTyrLysAsnLeuIle   961
AATGCTGGGGCAGCAGCTCTGGGAGCAGCAGCCGCAGCGATGCTCTAGCAGCAGATGCCCTAGCAAAGCCAAAGCAGATGCCCTTAAGAATTCAACAAATATGGAGTAAGTGACTATTACAAGAATCTAATC
                         A1 >
                       !! a1 >

AsnAsnAlaLysThrValGluGlyValLysAspLeuGlnAlaGlnValValGluSerAlaLysLysAlaArgIleSerGluAlaThrAspGlyLeuSerAspPheLeuLysSerGlnThr       1081
AACAATGCCAAAACTGTTGAAGGCGTAAAAGACCTTCAAGCACAAGTTGTTGAATCAGCGAAGAAAGCGCGTATTTCAGAAGCAACAGATGGCCTTATCTGATTTCTTGAAATCACAAACA
                  !! A2 >
                 !! a2 >

ProAlaGluAspThrValLysSerIleGluLeuAlaGluAlaLysValLeuAlaAsnArgGluLeuAspLysTyrGlyValSerAspTyrHisLysAsnLeuIleAsnAsnAlaLysThr       1201
CCTGCTGAAGATACTGTTAAATCAATTGAATTAGCTGAAGCTAAAGTCTTAGCTAACAGAGAACTTGACAAATATGGACTTATCAGACTATCAACAAGAACCTAATCAACAATGCCAAAACT

ValGluGlnValLysAspLeuGlnAlaGlnValValGluSerAlaLysLysAlaArgIleSerGluAlaThrAspGlyLeuSerAspPheLeuLysSerGlnThrProAlaGluAspThr       1321
GTTGAAGGTGTAAAAGACCTTCAAGCACAAGTTGTTGAATCAGCGAAGAAAGCGCGTATTTCAGAAGCAACAGATGGCTTATCTGATTTCTTGAAATCACAAACACCTGCTGAAGATACT
             !! A3 >

ValLysSerIleGluLeuAlaGluAlaLysValLeuAlaAsnArgGluLeuAspLysTyrGlyValSerAspTyrTyrLysAsnLeuIleAsnAsnAlaLysThrValGluGlyValLys       1441
GTTAAATCAATTGAATTAGCTGAAGCTAAAGTCTTAGCTAACAGAGAACTTGACAAATATGGAGTGACTATTACAAGAACCTAATCAACAATGCCAAAACTGTTGAAGGTGTAAAA
```

FIG 9

```
AlaLeuIleAspGluIleLeuAlaAlaLeuProLysThrAspThrTyrLysLeuIleLeuAsnGlyLysThrLeuLysGlyThrThrGluAlaValAspAlaAlaThrAlaGlu
GCACTGATAGATGAAATTTTAGCTGCACTACCTAAGACTGACACTTACTGTAAGCTTATCCTAATCCTTAATGCATTAAAGCATGTAAAGGCAAACATTGAAGCTGTTGATGCTGCTACTGCAGAA    1561
                                                                     B1

LysValPheLysGlnTyrAlaAsnAspAsnGlyLysValAspGlyValAspGlyGluTrpThrTyrLysThrPheThrValThrGluLysThrAlaAspAlaSerGluLeuThr
AAAGTCTTCAAACAATACGCTAACGACAACGGTGTTGACGGTGAATGGACTTACAAGACCTTTACAGTTACTGAAAAACCAGAAGTGATCGATGCGTCTGAATTAACA                      1681
                                                                        B1                                  b

ProAlaValThrThrTyrLysLeuValIleAsnGlyLysThrLeuLysGlyThrThrThrGluAlaValAspAlaAlaThrAlaGluLysValPheLysGlnTyrAlaAsnAspAsn
CCAGCCGTGACAACTTACAAACTTGTTATTAATGGTAAACATTGAAAGGCAAACACTACTGAACTGTGATGCTGCTACTGCAGAAAAGTCTTCAAACAATACGCTAACGACAAC                1801
                            B3                                                                                      b

GlyValAspGlyGluTrpThrTyrAspAspThrLysThrPheThrValThrGluLysProGluValIleAspAlaSerGluLeuThrProAlaValThrThrTyrLysLeuValIle
GGTGTTGACGGTGAATGGACTTACGACGATACGAAGACCTTTACAGTTACTGAAAAACCAGAAGTGATCGATGCGTCTGAATTAACACCAGCCGTGACAACTTACAAACTTGTTATT              1921
                                              B3                          b                                             B2

AsnGlyLysThrLeuLysGlyGluThrThrThrLysLeuAlaValAspAlaValAlaGlyGlyAspGluLysAlaPheLysGlnTyrAlaAsnAspAsnGlyValAspGlyValAspTrpTyrAspAsp
AATGGTAAACATTGAAAGGCGAAACAACTACTAAGCTAGCAGTAGACGCAGAAAACTGCAGAAAAAGCCTTCAAACATACGCTAACGACAACGGTGTTGATGGTGTTTGGACTTATGATGAT          2041
                                                                                                                    B2

AlaThrLysThrPheThrValThrGluMetValThrGluValProGlyAspAlaProThrGluProGlnAlaSerIleProLeuValProLeuValProLeuValProAlaThrProIle
GCGACTAAGACCTTTACGGTTACAGAGGTTACGAGTGTTCCTGGTGATGCACCAGAGCCTCAACAAGCAAGTATCCCCTTGTTCCGTTAACTCCTGCAACTCCAATT                         2161
                                                                                                            B2

AlaLysAspAlaLysAspThrLysLysGluAlaLysLysProGluAlaLysLysGluAlaLysLysAlaGluThrLeuProThrThrGlyGluGlySerAsnPro
GCTAAAGATGCAAAGGATACTAAGAAAGAAGCTAAGAAGCCTGAAGCTAAGAAAGAAGCTAAGAAAGCGGAAACTTTGCCAACTACAGGAGAAGGAAGCAACCCA                          2261

PhePheThrAlaAlaAlaLeuAlaValMetAlaGlyAlaLeuAlaAlaSerLysArgLysGlyAspEND
TTCTTCACAGCAGCTGCCCTTGCAGTAATGGCTGGCCGGTTGCGCGGGTGCTTTTGGCGTCCTTGCAGTAATGGCTGGTGCGGGT                                             2385
```

*FIG.9A*

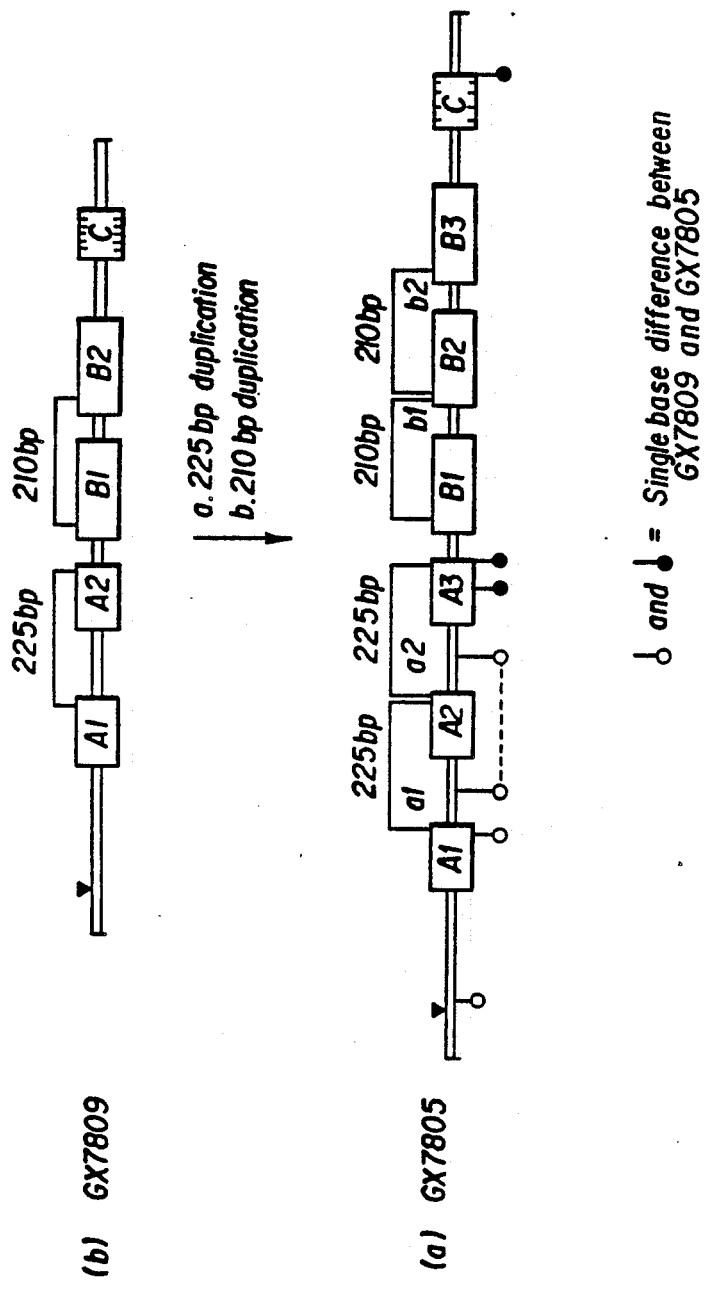
Fig. 10 THE STRUCTURE OF PROTEIN G GENES FROM STREPTOCOCCUS STRAINS GX7805 AND GX7809

CLONED STREPTOCOCCAL GENES ENCODING PROTEIN G AND THEIR USE TO CONSTRUCT RECOMBINANT MICROORGANISMS TO PRODUCE PROTEIN G

CROSS REFERENCE TO RELATED APPLICATIONS

This application is a division of Ser. No. 063,959, filed 6/19/87, which is a continuation-in-part of International Application PCT/US87/00329 filed Feb. 17, 1987 which is a continuation-in-part of U.S. Application Ser. No. 854,887, filed Apr. 23, 1986, which is a continuation-in-part of U.S. Application Ser. No. 829,354, filed Feb. 14, 1986.

FIELD OF THE INVENTION

This present invention relates to the cloning of genes which specify the biosynthesis of Streptococcus Protein G and the use of organisms transformed with the cloned genes to produce Protein G and Protein G-like polypeptides.

BACKGROUND OF THE INVENTION

There has been a growing interest in recent years in bacterial $F_c$ receptors, molecules that bind to antibodies through a nonimmune mechanism. This binding is not to the antigen recognition site, which is located in the $F_{ab}$ portion of the antibody molecule, but to the $F_c$ portion of the antibody. The $F_c$ region is common to many types of antibodies, thus bacterial $F_c$ receptors can bind to many types of antibodies. This property makes bacterial $F_c$ receptors useful in a number of immunochemical applications.

Bacterial $F_c$ receptors have a number of useful or potentially useful applications, primarily in the detection of antibodies, the purification of antibodies and the treatment of diseases. The detection of antibodies is required in several phases of laboratory research in immunology, including the screening of hybridoma clones for the secretion of specific monoclonal antibodies, the measurement of the immune response of an immunized animal, and the quantitation of antigens by competitive binding assays. Methods for detecting antibodies using bacterial $F_c$ receptors have been found to be more sensitive and less prone to interference and high background signals than other detection methods [Boyle, M.D.P., Biotechniques 2:334–340 (1984)].

$F_c$ receptors also are useful in purifying antibodies to be used in the purification of protein drugs and as therapeutics. Although a number of methods are known, a popular method involves the use of affinity chromatography on columns of immobilized bacterial $F_c$ receptors. This method is preferred because the columns can be reused many times, thus lowering the expense of purification.

A number of potential clinical uses of bacterial $F_c$ receptors are currently under investigation. They include passing plasma over extracorporeal columns of immobilized $F_c$ receptors, then reinfusing the treated plasma. See, for example, Tenan, D. S., et al., *N. Eng. J. Med.* 305:1195–1200 (1981).

The best known bacterial $F_c$ receptor is Protein A of *Staphylococcus aureus*, which binds to the constant $F_c$ domain of immunoglobulin IgG. Other bacterial $F_c$ receptors also have been identified. One of these is known as Protein G of Group G streptococci. Although Protein G is analogous to Protein A, Protein G has several important advantages. For example, Protein G binds to all subclasses of human IgG, whereas Protein A does not bind to the IgG3 subclass [Reis, K. J. et al. *J. Immunol.* 132:3098–3102 (1984)]. Protein G also is specific for IgG and does not cross-react with human antibodies of type IgA and IgM as Protein A does. [Myhre, E. B. and Kronvall, G. "Immunoglobulin Specificities of Defined Types of Streptococcal Ig Receptors" *In: Basic Concepts of Streptococci and Streptococcal Diseases;* J. E. Holm and P. Christensen, eds.; Redbook, Ltd., Chertsey, Surrey; pp. 209–210 (1983)]. In addition, Protein G binds to certain animal IgGs to which Protein A binds weakly or not at all. These include bovine, ovine, and caprine IgGI and several subclasses of equine IgG (Reis, K. J. et al., sucra). Protein G also has been found superior to Protein A in binding to several subclasses of murine monoclonal antibodies [Bjorck, L. and Kronvall, G. *J. Immunol.* 133:969–974 (1984)]. For these reasons, Protein G is likely to become the bacterial $F_c$ receptor of choice in a variety of applications.

Currently, Protein G is obtained by investigators for study by purification from Streptococcal strains which naturally produce it. For example, Streptococcal cells have been treated with proteolytic enzymes (e.g., papain or trypsin) to solubilize the Protein G (which is a cell wall protein), followed by known protein purification procedures (e.g., ion exchange chromatography, gel filtration, and affinity chromatography) to further purify the Protein G (European Patent Application, Publication Number 0 131 142).

Given the advantages, uses and potential uses of Protein G, it would be desirable to be able to produce the protein using recombinant DNA methodology. Accordingly, it is an object of the present invention to clone the gene encoding Protein G and to produce Protein G by transforming a microbial host with the cloned gene and cultivating the host under Protein G-producing conditions.

SUMMARY OF THE INVENTION

The present invention provides a cloned gene encoding an $F_c$ receptor protein having the IgG binding properties of Protein G. The gene is derived from a *Streptococcus Sp.*, Lancefield Group G, strain and inserted onto a cloning vector. Cells of a prokaryotic organism which have been stably transformed with recombinant vectors are disclosed. One transformed strain comprises a first vector carrying the gene encoding a protein having the properties of Protein G and a second vector which does not contain the gene and acts as a cryptic helper plasmid to stably maintain the first vector in the host strain. Other transformants carry vectors in which the DNA insert comprising the gene encoding the Protein G protein has been modified such that a helper plasmid is no longer needed. The transformed strains are cultivated under Protein G-producing conditions.

The invention further provides the identification of the nucleotide sequence and amino acid sequence for the active binding site of the molecule. One gene cloned by the inventor contains two active sites. A second cloned gene contains three active sites.

The invention further provides for the production, using recombinant vectors, of Protein G-like polypeptides, the Protein G-like polypeptides containing one or more amino acid sequences which demonstrate the IgG-binding characteristics of Protein G.

BRIEF DESCRIPTION OF THE FIGURES

FIGS. 3 and 3A-C show a DNA sequence for the Protein G gene, as well as the amino acid sequence encoded by the gene.

FIGS. 8 and 8a-c show the location of the active sites, B1 and B2, on Protein G as coded for by the cloned Protein G gene derived from streptococcus GX7809.

FIGS. 9 and 9a show the DNA and amino acid sequences for the cloned Protein G gene derived from streptococcus GX7805. This gene codes for a Protein G containing three active sites.

FIG. 10 shows the relationship between the repeating structures of the Protein G gene derived from strains GX7805 and GX7809.

DETAILED DESCRIPTION OF THE PREFERRED EMBODIMENTS

Figure 1:
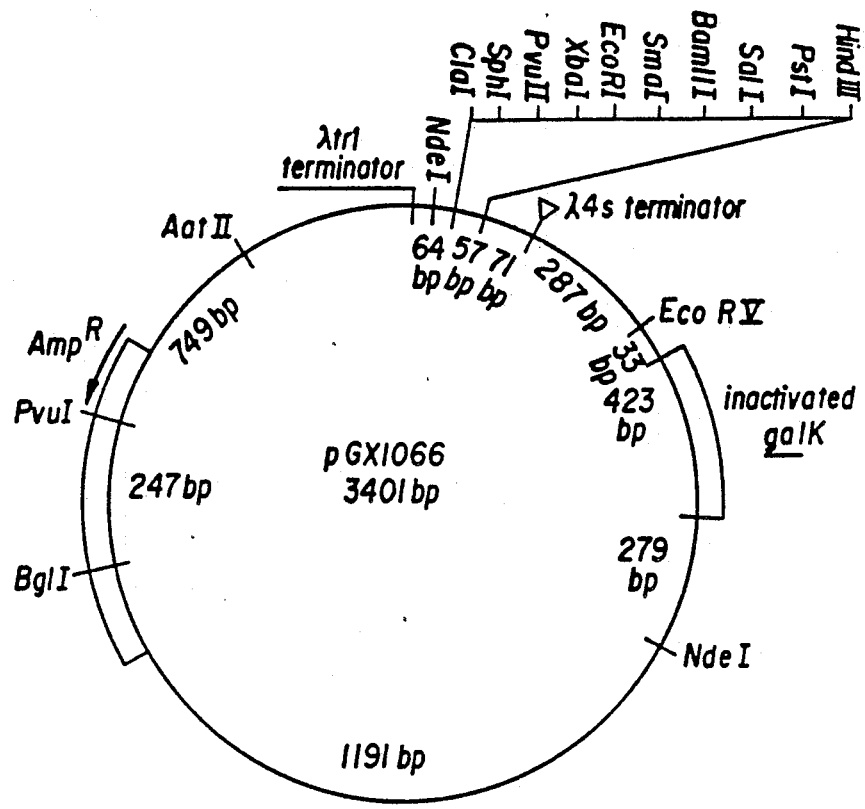
FIG. 1 is a diagram showing the salient features of plasmid pGX1066, a vector suitable for use in cloning a Protein G-encoding DNA fragment.

The present invention relates to cloned Protein G genes. A DNA fragment comprising a Protein G gene is isolated from a *Streptococcus Sp.* Lancefield Group G, strain and inserted into a cloning vector. Another aspect of the invention relates to production of Protein G by transforming host cells with a recombinant vector comprising a cloned Protein G gene and culturing the transformed cells under protein-producing conditions, whereupon Protein G is produced by the cells.

Yet another aspect of the invention is directed to production of a Protein G-like material, said material containing from one to twenty Protein G binding sites per molecule. This Protein G-like material has the formula:

$$-(-B-b-)_n-$$

wherein B is B1, B2 as shown in FIG. 9 or a hybrid sequence comprising B1 and B2 which is designated B3, b is as shown in FIG. 8, and n is from 1 to 20.

By the term "hybrid sequence" is intended DNA or amino acid sequences which contain portions of the respective sequences corresponding to B1 and B2 and which retain the immunoglobulin binding properties of Protein G. Such a hybrid sequence is shown in FIG. 9 and is labeled B3. This hybrid sequence comprises the portion of B1 corresponding to the amino acid sequence 298-314 of B2 fused to the sequence 245-282 of B1. Thus, it is intended that all such hybrid sequences which retain the immunoglobulin binding properties of Protein G are within the scope of this invention.

Cloning of the Protein G gene and production of Protein G in bacterial hosts, such as *E. coli* or *Bacillus subtilis*, through recombinant DNA technology, according to the methods of the present invention, provides a number of advantages over current methods for obtaining the protein. By the method of this invention, relatively high levels of microbial Protein G production can be obtained, the protein can be produced under conditions where it can be isolated more favorably, and the protein can be produced in a non-pathogenic host. The cloned gene may be inserted into various multicopy expression vectors to give enhanced levels of this valuable IgG-binding protein in cultured *E. coli* cells transformed with the recombinant expression vectors. Production of Protein G in *E. coli* or *B. subtilis* cells is preferable to cultivation of Protein G-producing Streptococcal strains, which are commonly pathogenic strains.

In addition, the proteolytic enzymes, such as papain and trypsin, which have been used to release Protein G from the cell wall of Streptococcal cells, may degrade the Protein G product. Thus, known methods of isolating Protein G from Streptococcal cells may produce low molecular weight degraded forms of Protein G.

The first step in the cloning of the Protein G gene, according to the present invention, is isolation of Streptococcal strains that produce Protein G. This may be done by assaying various strains for IgG binding activity using any suitable immunoassay technique. A technique used by the Applicant is the colony immunoassay described in detail in the examples section below. Strains found to have IgG-binding activity are next tested for the ability to bind IgG3 as well as unfractionated IgG, since the ability to bind IgG3 is a desired property associated with Protein G. A hemagglutination assay using red blood cells coated either with IgG3 or with unfractionated IgG (described in detail in the examples below) is a convenient method for identifying Protein G-producing strains. A known Protein A-producing strain, such as *Staphylococcus aureus* Cowan I [Sjoquist, J., *Eur. J. Biochem.*, 78: 471-490 (1977)], may be used as a control, since Protein A binds unfractionated IgG but not IgG3.

Chromosomal DNA is isolated from strains found to produce Protein G by cultivating the strains in a nutrient medium to a desired cell density, then lysing the cells by any of the conventional chemical, mechanical, and/or enzymatic methods known in the art. Conventional extraction and precipitation procedures are used to isolate the chromosomal DNA. Fragments of DNA of a suitable size for cloning are obtained by such known mechanical methods as sonication or high-speed stirring in a blender, or by enzymatic methods, such as partial digestion with DNAseI, which gives random fragments, or with restriction endonucleases, which cleave at specific sites.

The chromosomal DNA fragments then are inserted into a cloning vector. Any suitable plasmid or bacteriophage cloning vector may be used. For a vector to be suitable, it should have several useful properties. It should have an origin of replication that is functional in the intended microbial host cells, and a selectable marker (such as an antibiotic resistance gene) to aid in identification of host cells that have been transformed with the vector. It should be able to accept inserted DNA fragments and still replicate normally. Preferably, the vector comprises one or more unique restriction endonuclease recognition sites at which DNA fragments can be inserted without destroying the vector's ability to replicate.

Suitable cloning vectors include phage derivatives such as lambda gt11 [Young and Davis, *Proc. Nat'l Acad. Sci. U.S.A.*, 80:1194–1198 (1983)], the various phage M13-derived vectors such as M13mp9 (commercially available from Bethesda Research Laboratories), plasmids such as pBR322, and many others [Old and Primrose, *Principles of Gene Manipulation.* 2nd. Ed., Univ. of Calif. Press, pgs. 32–35 and 46–47 (1981)]. The Applicant used a pBR322-derived plasmid vector pGX1066, shown in FIG. 1.

The Streptococcal DNA is inserted into the cloning vector by such methods as homopolymeric tailing or by using linker molecules (Old and Primrose, supra at page 92). Advantageously, the vector is linearized with a restriction endonuclease, and the chromosomal DNA is also digested with a restriction endonuclease that produces DNA fragments that are ligatable to the ends of the linearized vector molecule. The Streptococcus-derived DNA fragments are thus advantageously inserted into the cloning vector in a standard reaction using the enzyme T4 DNA ligase.

Bacterial cells are transformed with the recombinant cloning vector, using standard procedures, and the bacterial colonies are screened for production of Protein G. Assays such as the colony immunoassay and the hemagglutination assay described in the examples below are suitable for identification of recombinant strains producing Protein G. As described more fully in Example I below, the initial positive colony identified was unstable. Through purification procedures in which this clone underwent several rounds of restreaking, a derivative of the clone was obtained which appeared stable and produced Protein G. This strain was designated *E. coli* GX7820.

Plasmid DNA from this strain was isolated and then analyzed by restriction analysis followed by gel electrophoresis. It has been determined that the strain contains two plasmids. One, designated pGX1066X, appears to be approximately the same size as the pGX1066 cloning vector; the other, designated pGX4530, appears to be pGX1066 containing an 11 kilobase-pair (kbp) insert. Although the Applicant does not wish to be bound by a particular theory, it appears, as illustrated more fully in the examples, that pGX1066X is a "cryptic helper plasmid", a derivative of pGX1066 in which the ampicillin resistance gene is no longer intact. The original transformant strain probably contained pGX1066 and pGX4530, and was unstable because pGX4530 was lost from the cells due to lack of selective pressure to retain that plasmid when pGX1066 was present to provide ampicillin resistance. Once pGX1066X appeared, having a mutation that inactivated its ampicillin resistance gene, only those host cells which had retained pGX4530 (having an intact ampicillin resistance gene) could survive on the ampicillin plates. Plasmid pGX1066X is retained in the cells containing both plasmids, presumably because it serves to limit the copy number of pGX4530 in the cell. Plasmid pGX4530 alone is lethal to the host cells (see Example I), but the presence of pGX1066X in the same host cell reduces the copy number of pGX4530 to a tolerable level. The plasmids are from the same "incompatibility group", i.e., the plasmids compete with each other for maintenance in the cell, so that each plasmid limits the copy number of the other in the host cell. *E. coli* strain GX7820 has been deposited with the American Type Culture Collection in Rockville, Md., and given accession number 53460.

An *E. coli* strain was transformed with a mixture of the plasmids isolated from strain GX7820. The tranformation resulted in a number of tiny, strongly positive colonies with a few (about 20%) resembling GX7820. From these tiny positive colonies have been isolated two stable variants which do not carry the helper plasmid and which are more strongly positive for Protein G than the original GX7820. One strain, designated GX7823, carries a plasmid (pGX4533) from which has been deleted a two kilobase pair (kbp) fragment of the insert in the pGX4530 plasmid. *E. coli* strain GX7823 has been deposited with the American Type Culture Collection in Rockville, Md. and given accession number 53461. The other, designated GX7822, carries a plasmid which has acquired a three kbp insert of DNA within the original insert at a site very close to one end of the deletion in the plasmid carried by the GX7823 strain. The Protein G gene has been located on a 1.9 kilobase pair (kbp) fragment of the Streptococcal DNA insert on pGX4533.

To improve Protein G production levels, the cloned Protein G gene may be inserted into a variety of expression vectors. The expression vectors comprise "regulatory regions", which include DNA sequences necessary for gene expression, i.e., the transcription of DNA into mRNA followed by translation of the mRNA into the protein that the gene encodes. The Protein G gene may contain its natural expression signals, or those signals may be removed and the structural portion of the cloned Protein G gene (i.e., the protein-encoding portion of the gene) can be operably fused, in accordance with conventional methods, to other expression signals, contained in an expression vector, which are capable of directing the Protein G gene in the chosen host organism. For example, when the host microorganism is *E. coli*, the expression vector may comprise such known regulatory regions as the trp promoter/operator, the lac promoter/operator, the bacteriophage lambda $P_L$ promoter/operator, and many others.

In one embodiment of the invention, the expression vector further comprises a DNA sequence homologous to a region of the chromosome of the host microorganism. This construction permits linear integration of the vector into the host chromosome in the region of homology. An advantage to this method is that there is less likelihood of loss of the Protein G sequence from the host, due to negative selection favoring vector-free cells.

Protein G may be produced at high levels in bacterial cells transformed with such recombinant expression vectors. In addition, production of Protein G within the cell may be controlled by using promoter/operator systems which may be induced (to begin gene expression) at a desired cell density, or in which gene expression can be reversibly repressed until the cell density in a culture of recombinant bacterial cells has reached a desired level. The potentially negative effects on cell growth of production of a heterologous protein can thus be avoided.

Transformed cells containing a cloned Protein G gene are cultivated under protein-producing conditions such that Protein G is produced by the cells. Cultivation conditions, including large-scale fermentation procedures, are well known in the art. The cells may be cultivated under any physiologically-compatible conditions of pH and temperature, in any suitable nutrient medium containing assimilable sources of carbon, nitrogen and essential minerals that supports cell growth. Protein-producing cultivation conditions will vary according to the type of vector used to transform the host cells. For example, certain expression vectors comprise regulatory regions which require cell growth at certain temperatures, or addition of certain chemicals to the cell growth medium, to initiate the gene expression which results in production of Protein G. Thus, the term "protein producing conditions" as used herein is not meant to be limited to any one set of cultivation conditions.

Advantageously, the cloned gene is transferred to *B. subtilis* by methods previously applied to the gene encoding Protein A and described in commonly assigned U.S. Pat. No. 4,617,266 (1986), incorporated herein by reference in its entirety. In accordance with these methods, Protein G can be synthesized in *B. subtilis*.

The functionally active portions of Protein G was localized to a repeating structure by examining the IgG-binding activity of protein produced by *E. coli* strains carrying modified forms of the cloned protein G gene. Thus, the invention also relates to a cloned gene which encodes one or more of the functionally active portions of Protein G and to the protein so produced which has the immunoglobulin binding properties of Protein G. The details of the identification and isolation of the gene coding for the active site of Protein G are set forth in Example III below. The DNA sequences, and the amino acid sequences encoded thereby, of two genes encoding, respectively, two and three active sites per Protein G molecule are set forth in FIGS. 8 and 9. With this information, it is now possible to produce Protein G-like molecules which contain multiple sites of Protein G activity. Synthetic genes may be constructed, utilizing known synthetic procedures, which code for from one to twenty or more active sites within a given amino acid sequence, thereby providing higher binding efficiency and capacity to the resulting material. A preferred Protein G-like material contains 1 to 10 active sites; a more preferred material contains 1 to 5 active sites.

Also within the scope of this invention are proteins having the immunoglobulin-binding properties of Protein G, further having deletions or substitutions of amino acids or additional amino acids at the amino or carboxyl terminus thereof.

Preferred forms of Protein G are encoded by genes from which coding sequences upstream and downstream from the active sites (B1 and B2) have been deleted. The details regarding the deletion of such coding sequences are set forth in Examples IV, VI and VII, below. However, it will be recognized by one skilled in the art that additional deletions and structural modifications can be constructed by analogous methods. It will further be recognized that various upstream deletions and various downstream deletions can be recombined in vitro in different combinations to produce novel gene structures. Such recombination can be facilitated by the use of unique restriction endonuclease sites for SmaI (upstream from the apr promoter), KpnI (immediately upstream from sequences encoding domain B1) and HindIII (downstream from the coding sequences), by assorting SmaI-KpDI fragments and KonI-HindIII fragments. Novel combinations constructed in this way retain sequences encoding the B domains, and therefore retain the IgG-binding activity of Protein G. Additionally, it will be recognized that the SmaI-BamHI fragment of these plasmids which carries the apr promoter and signal-encoding sequences can be replaced by analogous fragments carrying other promoters and signal-encoding sequences that are active in promoting synthesis and secretion of foreign proteins in *B. subtilis*.

Any suitable known method of protein purification may be used to recover and purify the Protein G from the host cells. The cells may be lysed, if necessary, using known chemical, physical, and/or enzymatic means. The Protein G then may be purified from the cell lysate using such standard procedures as adsorption to immobolized immunoglobulin, as described by Sjoquist, U.S. Pat. No. 3,850,798 (1974), ion-exchange or gel chromatography, precipitation (e.g., with ammonium sulfate), dialysis, filtration, or a combination of these methods.

The following Examples are provided to illustrate the invention, and is not to be construed as limiting the scope of the invention.

EXAMPLE I

Cloning a Streptococcus Protein G Gene into *E. coli*

Streptococci of Lancefield group G were obtained from hospitals, and 11 independent isolate strains were derived from the clinical isolates. Each strain was assayed for ability to bind IgG using the following colony immunoassay procedure. The strains were streaked on L-Broth-agar plates which had been overlaid with a sheet of nitrocellulose and (top layer) a sheet of cellulose acetate ("immunoassay plates"). The plates were incubated at 37° C. until bacterial colonies were visible on the cellulose acetate sheet.

The nitrocellulose sheets then were removed from the plates, and IgG-binding proteins were detected on the sheets using an immunochemical procedure, as follows. The sheets were first treated with bovine serum albumin (3.0% w/v in "Tris-saline", which comprises 0.01M Tris-HCl, pH 8.0, and 0.15M NaCl) to block nitrocellulose sites to minimize non-specific binding of antibodies to the nitrocellulose in subsequent steps. The sheets then were treated with normal rabbit serum (diluted 1:1000 in Tris-saline containing 3% w/v bovine serum albumin) for 1 hour at 23° C., followed by peroxidase-conjugated goat anti-rabbit IgG (similarly diluted), and, finally, with 4-chloro-1-naphthol (0.6 mg/ml) and hydrogen peroxide (0.06% w/v in Tris-saline containing 0.2 volume methanol), washing the sheets with Tris-saline between incubation steps. Blue spots on the nitrocellulose sheet indicate the presence of IgG-binding protein, and the blue areas correspond to microbial colonies which produced the IgG-binding protein.

Nine of the strains were positive, i.e. were found to bind IgG, although to varying degrees. Several of the strains were next tested for ability to bind IgG3, using the following hemagglutination assay. Sheep red blood cells (RBC) (Cappel Laboratories, Malvern, Penna.) were coated with immunoglobulin essentially as described by Adler and Adler [*Meth. Enzymol.* 70:455–466 (1980)]. RBC were washed with phosphate-buffered saline (PBS, containing 8.4 g/l NaCl, 1.1 g/l Na$_2$HPO$_4$, and 0.27 g/l NaH$_2$PO$_4$) and treated for 15 min. at 37° C. with a solution of tannic acid at 2.5 mg/ml in PBS. Cells were recovered by centrifugation and resuspended in PBS containing, at 0.2 mg/ml, either (a) total human immunoglobulin G (available from Sigma Chemical Co; St. Louis, Mo.), (b) IgG3 myeloma protein or (c) PBS only. After incubation at 37° C. for 30 min, RBC were recovered by centrifugation and washed with PBS. For the agglutination assay, 50 ul of a 1% suspension of coated RBC were mixed with 50 ul of a test cell extract, diluted serially in PBS, in a conical well of a multiwell dish. Unagglutinated RBC settle to the bottom of the well and form a small pellet, while agglutinated RBC form a more diffuse precipitate on the walls of the well.

Each of the positive group G Streptococcal strains agglutinated IgG3-coated erythrocytes as efficiently as erythrocytes coated with unfractionated IgG, which is expected for Protein G-producing strains. In contrast, *Staphylococcus aureus* Cowan I cells, a strain which produces Protein A, agglutinated red blood cells coated with unfractionated IgG, but showed no activity toward IgG3-coated cells, as expected. None of the cells agglutinated red blood cells which had been incubated with PBS only, i.e., uncoated red blood cells.

The same hemagglutination assay then was performed on supernatant fractions and cell extracts from cultures of the Streptococcus isolates and the isolates appeared to have differing localization of the IgG-binding activity. In some strains the activity appeared to be predominantly cell-bound, in some it was found predominantly in the culture supernatant, and some strains were intermediate. Three strains, which had differing localization of the IgG-binding activity, were chosen as sources of DNA for cloning the Protein G gene.

Cells from each strain were cultivated in 250 mls. of Todd-Hewitt broth (commercially available from Fisher Scientific, Richmond, Va.) containing 20mM D,L-threonine. After 4 hours of cultivation, glycine was added to a final concentration in the culture medium of 5% (w/v). The cells were harvested by centrifugation after 5 hours of cultivation, when the cell density had reached an absorbance at 600 nm of about 0.5 to 1.0. The cell pellets were washed with PBS and then frozen in liquid nitrogen and stored at −70° C. After thawing, the cells were washed with, and then resuspended in, 10 mls of S7 medium [described by Vasantha and Freese, *J. Bacteriology* 144:1119–1125 (1980)] containing 0.5 M sucrose, to which 200 ul of 5 mg/ml mutanolysin (commercially available from Sigma Chemical Co.) had been added. Following incubation at 37° C. for 45 minutes, the resulting protoplasts were pelleted by centrifugation, and then lysed osmotically by resuspension in a solution containing 100mM EDTA, pH 8.0, 150 mM NaCl, and 0.5 mg/ml Proteinase K. Following incubation at 37° C. for 55 minutes, alpha-toluenesulfonyl fluoride (also called phenylmethanesulfonyl fluoride or PMSF, and available commercially, e.g. from Sigma) was added to a final concentration of 2 mM, and the mixture was incubated at 70° C. for 15 minutes to inactivate the Proteinase K. The cell lysate was extracted three times with chloroform/isoamyl alcohol (24:1) to further remove proteins, and an equal volume of isopropanol was added to the aqueous phase to precipitate the DNA. The precipitated DNA was collected by winding on a spool, and then was washed with 70% ethanol and dried in vacuo.

The DNA pellets (from each of the 3 strains) were each resuspended in 0.5 ml of a 0.01M Tris-HCl (pH 7.8)/lmM EDTA/0.05 M NaCl solution. A portion of this isolated chromosomal DNA was partially digested with the restriction endonuclease MboI (commercially available) by adding 2 units of MboI to 25 ul of the resuspended DNA in 100 ul of a buffer containing 100 mM Tris-HCl, pH 7.8, 150 mM NaCl and 10 mM MgCl$_2$. The reaction mixture was incubated at 37°'C. for 13 minutes, then at 7020 C. for 10 minutes. The digested DNA was subjected to electrophoresis on a 0.8% agarose gel for 15 hours at 0.35 volts/cm. The section of the gel containing DNA fragments between about 4 and 9 kilobase-pairs (kbp) in length was excised from the gel and crushed to aid in recovery of the DNA. An equal volume of H$_2$O-saturated phenol was added to the crushed gel portion, and the mixture was frozen at −70° C. for 1 hour. Without prior thawing, the mixture was centrifuged at room temperature for 15 minutes in an Eppendorf microfuge, and the aqueous phase was extracted twice with an equal volume of phenol and once with an equal volume of phenol/chloroform/isoamyl alcohol (25:24:1). The DNA was precipitated from the aqueous phase by adding 2.5 volumes of 95% ethanol and 30 ug glycogen as a carrier.

The cloning vector into which the chromosomal DNA fragments were inserted was plasmid pGX1066, shown in FIG. 1. This plasmid comprises a bank of closely-spaced restriction endonuclease recognition sites useful for insertion of DNA fragments to be cloned. The bank of cloning sites is bordered by two transcription terminators. *E. coli* strain GX 1186, which constitutes strain GX1170 transformed by plasmid pGX1066 has been deposited with the ATCC as No. 39955. 3 ug of plasmid pGX1066 DNA were digested with the restriction endonuclease BamHI (commercially available and used according to manufacturer's specifications.) The digested plasmid DNA then was treated with 1 unit calf intestine alkaline phosphatase, (obtained from Boehringer-Mannheim and used according to manufacturer's specifications) for 30 minutes at 37° C. Following extraction of the reaction mixture with phenol/chloroform/isoamyl alcohol (25:24:1), the DNA was precipitated by adding 0.1 volume 2M sodium acetate, 10 mM EDTA, and 2.5 volumes 95% ethanol and 10 ug glycogen as a carrier. 0.5 ug of the pGX1066 vector DNA (BamHI-digested and phosphatase-treated) then was ligated to 0.2 ug of the partially MboI digested Streptococcus chromosomal DNA prepared above. The 10 ul reaction mixture contained 1 unit of T4 DNA ligase (commercially available and used according to manufacturer's instructions) and was incubated at 4° C. for 20 hours.

*E coli* SK2267 (F− cal thi Tl$^r$ hsdR4 endA sbcB15. available from the *E. coli* Genetic Stock Center, Yale University, New Haven, Conn.) cells were made competent for transformation by standard calcium chloride treatment, and 0.25 ml of the competent cells then were mixed with 20 ul of the ligation mixture in a standard transformation procedure [Lederberg and Cohen, *J. Bacteriol.* 119:1072–1074 (1974]. The cells then were pelleted by centrifugation and resuspended in 0.3 ml L Broth. 0.1 ml of cells then were plated on each of three L Broth-agar plates containing 100 ug/ml ampicillin, which had been overlaid with a sheet of nitrocellulose and (top layer) a sheet of cellulose acetate (immunoassay plates). The plates were incubated at 37° C. until bacterial colonies were visible on the cellulose acetate sheet.

The nitrocellulose sheets then were removed from the plates, and IgG-binding proteins were detected on the sheets using the immunochemical procedure described above. The sheets were first treated with bovine serum albumin (3.0% w/v in tris-saline) to block nitrocellulose sites to minimize non-specific binding of antibodies to the nitrocellulose in subsequent steps. The sheets then were treated with normal rabbit serum, diluted 1:1000 in Tris-saline containing 3.0% w/v bovine serum albumin, for 1 hour at 23° C., followed by peroxidase-conjugated goat anti-rabbit IgG (diluted similarly), and, finally, with 4-chloro-1-naphthol (0.6 mg/ml) and hydrogen peroxide (0.06% w/v in Tris-saline containing 0.2 vol. methanol), washing with tris-saline between incubation steps.

One positive colony was identified, and was located on a plate containing transformants derived from Streptococcus strain GX7809 (one of the three Streptococcus strains from which DNA was isolated for cloning.) The positive colony was streaked out on an immunoassay plate (containing 100 ug/ml ampicillin, as above) to obtain a purified transformant strain. The nitrocellulose sheet was processed as above, and only a few positives were found among hundreds of negative colonies. It appeared that the original transformant was unstable, so the restreaking process was repeated, and only one positive was found among hundreds of negative colonies. Another round of restreaking produced a plate containing mostly positive colonies. One of the positive colonies, a derivative which was apparently more stable than the original positive transformant, was isolated and designated $E.$ $coli$ strain GX7820. Samples of $E.$ $coli$ GX7820 have been deposited at the American Type Culture Collection in Rockville, Md. and given the accession number ATCC No. 53460.

In addition to the original positive colony, several small but strongly positive spots, which could not be correlated with any colony, were observed. These spots yielded no positive progeny on restreaking.

A standard procedure was used to isolate plasmid DNA from $E.$ $coli$ GX7820, and the plasmid DNA was analyzed by restriction analysis followed by gel electrophoresis. The strain was found to contain two types of plasmids. One plasmid (designated pGX1066X) appeared to be the same size as the pGX1066 cloning vector, while the other (designated pGX4530) apparently was pGX1066 containing an 11 kbp insert. Competent $E.$ $coli$ SK2267 cells then were retransformed with the mixture of plasmids isolated from GX7820, and transformants were selected on immunoassay plates containing 100 ug/ml ampicillin. Positive transformants of two types were obtained. A majority formed tiny, strongly positive colonies, most of which could not be propagated. A minority resembled GX7820 in being of more normal size and more easily propagatable. In order to clarify the cause of these results, competent $E.$ $coli$ SK2267 cells were also transformed with gel purified plasmids, as follows:

Transformation A: pGX4530 alone
Transformation B: pGX1066X alone
Transformation C: mixture of pGX4530 and pGX1066X The results were as follows:

Transformation A: tiny, strongly positive colonies, most of which could not be propagated.
Transformation B: no transformants
Transformation C: many tiny, strongly positive non-propagatable colonies (as in trans. A) with about 20% of the positives resembling GX7820, i.e. of normal size and propagatable.

Several of the tiny, strongly positive colonies were chosen from the retransformation plates above (i.e., the transformants resulting from transformation of $E.$ $coli$ with an unfractionated plasmid preparation derived from strain GX7820 comprising a mixture of pGX1066X and pGX4530) and were restreaked to isolate propagatable strains. Plasmid DNA was isolated from two strains, and both were found to have lost the pGX1066X helper plasmid. One strain (designated $E.$ $coli$ GX7823) contained a plasmid pGX4533 in which a deletion of about 2 kbp had occurred in the 11 kbp insert found in pGX4530. Samples of $E.$ $coli$ GX7823 have been deposited at the American Type Culture Collection in Rockville, Md. and given the accession number ATCC No. 53461. The second strain (designated $E.$ $coli$ GX7822) contained a plasmid pGX4532 which had acquired an additional 3 kbp of unidentified DNA inserted within the original 11 kbp insert, at a site very close to one end of the deletion in pGX4533.

The strains $E.$ $coli$ GX7823 (containing pGX4533) and $E.$ $coli$ GX7820 (containing pGX4530) were cultivated in L-Broth plus ampicillin. The cells were pelleted by centrifugation, lysed by incubating for 30 min at 37° C. in the presence of 0.5 mg/ml lysozyme in a buffer containing 50 mM EDTA, pH 8.0, and 2 mM PMSF. Samples of the extracts were prepared for electrophoresis by heating for 5 min. at 100° C. in the buffer described by Studier [$J.$ $Mol.$ $Biol.$ 79:237-248 [1973)], and the samples were subjected to electrophoresis on a 12.5% acrylamide-SDS gel as described by Studier, op cit., to separate the proteins. A standard electrophoretic (Western Blotting) technique was used to transfer the protein bands from the gel to nitrocellulose paper. The nitrocellulose was subsequently incubated (in sequence) with BSA, normal rabbit serum, peroxidase-conjugated goat anti-rabbit IgG, and 4-chloro-1-naphthol plus $H_2O_2$ (the same nitro-cellulose treatment as the immunochemical procedure described above). Both strains were found to produce the same IgG-binding protein bands with mobilities corresponding to molecular weights between approximately 90,000 to approximately 30,000 with a predominant band at 57,000.

Figure 2:
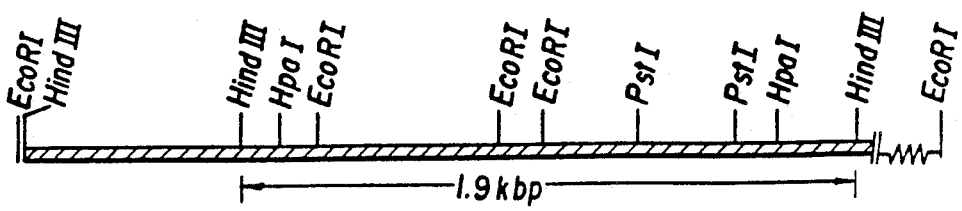
FIG. 2 shows a partial restriction map of plasmid pGX4533, a recombinant plasmid vector containing a Protein G-encoding DNA, fragment.

Plasmid pGX4533 was subjected to restriction analysis, and a partial restriction map is shown in FIG. 2. The single line represents the vector (pGX1066) sequences, while the hatched area represents the DNA that has been inserted into the plasmid vector and which contains the Protein G gene.

The 1.9 kbp HindIII fragment in the insert was subcloned into pGX1066, and the resulting recombinant plasmid (pGX4547) was transformed into $E.$ $coli$. Western blotting of the proteins produced by this transformant ($E.$ $coli$ GX7841) was done as described above, and the same IgG-binding protein bands were present including the predominant 57,000 band. The transformant was also analyzed in a hemagglutination assay, as described above. Extracts of the transformant agglutinated tanned sheep erythrocytes coated with IgG3 (human myeloma protein) and with unfractionated human IgG, but uncoated erythrocytes were not agglutinated. An extract from a Protein A-producing $E.$ $coli$ strain agglutinated the erythrocytes coated with unfractionated IgG, but not those coated with IgG3 or uncoated erythrocytes. A control *E. coli* strain which produced neither Protein A nor Protein G failed to agglutinate any of the erythrocyte samples.

These results demonstrate that *E. coli* strains GX7841, GX7820, and GX7823 produce IgG-binding protein having the properties which are characteristics of Protein G.

EXAMPLE II

DNA and Amino Acid Sequence Data

The DNA sequence of the cloned gene was determined. This sequence is shown in FIG. 3, along with the amino acid sequence specified by the DNA sequence. The data in FIG. 3 are for the entire 1.9 kbp HindIII fragment which contains the cloned Protein G gene, as described above.

It will be appreciated that because of the degeneracy of the genetic code, the nucleotide sequence of the gene can vary substantially. For example, portions or all of the gene could be chemically synthesized to yield DNA having a different nucleotide sequence than that shown in FIG. 3, yet the amino acid sequence would be preserved, provided that the proper codon-amino acid assignments were observed. Having established the nucleotide sequence of the Protein G gene and the amino acid sequence of the protein, the gene of the present invention is not limited to a particular nucleotide sequence, but includes all variations thereof as permitted by the genetic code.

The Protein G protein of the present invention is not limited to a protein having the exact amino acid sequence shown in FIG. 3. A protein comprising deletions or substitutions in the sequence shown in FIG. 3, or additional amino acids at the amino or carboxyl terminus of the protein, are included in the present invention as long as the protein retains the desired IgG-binding properties of Protein G, described above. These variations in amino acid sequence may be achieved by chemical synthesis of the gene, or by known in vitro mutagenesis procedures, for example.

The following abbreviations are used in FIG. 3:

| | |
|---|---|
| A = deoxyadenyl | |
| T = thymidyl | |
| G = deoxyguanyl | |
| C = deoxycytosyl | |
| GLY = glycine | CYS = cysteine |
| ALA = alanine | MET = methionine |
| VAL = valine | ASP = aspartic acid |
| LEU = leucine | GLU = glutamic acid |
| ILE = isoleucine | LYS = lysine |
| SER = serine | ARG = arginine |
| THR = threonine | HIS = histidine |
| PHE = phenylalanine | PRO = proline |
| TYR = tyrosine | GLN = glutamine |
| TRP = tryptophan | ASN = asparagine |

EXAMPLE III

Figure 4:
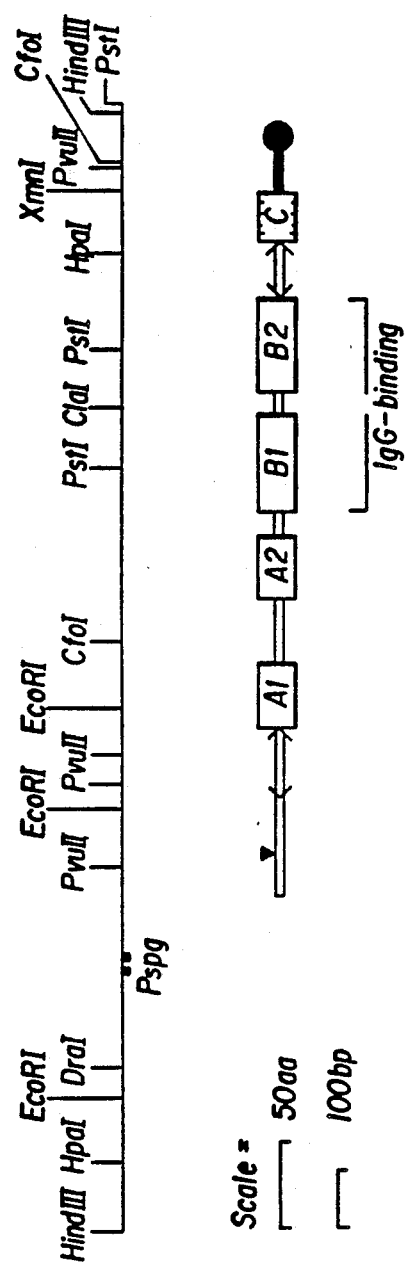
FIG. 4 shows the restriction map of the cloned protein G gene and the repeating structure of its protein product responsible for IgG-binding.

Identification of the Portions of the Protein G Molecule Responsible for the IgG-binding Activity By examining the IgG binding activity of protein produced by *E. coli* strains carrying deleted and modified forms of the cloned protein G gene, the activity was localized to the repeating structure between amino acid residues and 352 (FIG. 8). The amino acid sequences of regions B1 and B2 are identical at 49 of the 55 corresponding positions in each. This repeating structure is illustrated in FIG. 4, where it is indicated as B1 and B2.

Figure 5:
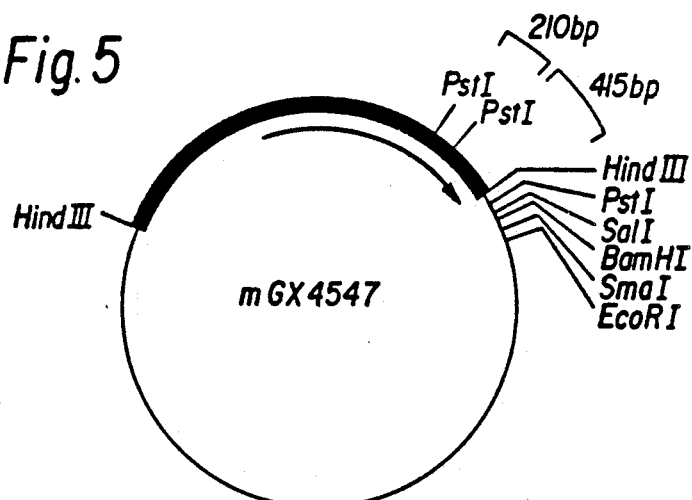
FIG. 5 shows the partial restriction map of mGX4547, a bacteriophage vector containing a Protein G-encoding fragment.

The 1.9 kbp HindIII fragment indicated in FIG. 2, which contains the entire coding sequence for protein G, originally isolated from Streptococcus GX7809, was subcloned in bacteriophage M13mp9 [Messing, J., *Methods Enzymol.* 101:20 (1983)]. The plasmid pGX4547 was digested with endonuclease HindIII, as was the double stranded replicative form of bacteriophage M13mp9 DNA. The latter was also treated with calf alkaline phosphatase (2 units in 15 ul), which was present during the digestion with HindIII, to prevent recircularization of the vector. After extraction with phenol and precipitation with ethanol, the two digested DNA preparations were mixed and incubated with DNA ligase under ligation conditions. The ligated DNA preparation was used to transfect *E. coli* strain GX1210 (F' traD36 proA+B+lacIq/delta-lacZM15 delta-(lac-pro) supE thi zig::Tn10 hsdR2). Transfected cells from plaques were screened for the production of protein G by colony immunoassay. One which produced a positive assay response was designated mGX4547, and was shown to have the partial restriction map illustrated in FIG. 5.

Double stranded replicative form DNA isolated from *E. coli* infected with mGX4547 was digested with endonuclease PstI. After extraction with phenol and ethanol precipitation, the digested DNA was incubated with DNA ligase under ligation conditions in dilute solution (approximately 5 ug digested DNA per ml). The religated DNA preparation was then used to transfect *E. coli* GX1210. Replicative form DNA was prepared from cells infected from several plaques, and the same infected cells were assayed for the production of IgG-binding protein by colony immunoassay. Several clones were found by analysis of RF DNA with restriction endonuclease PstI to have lost both the 210 bp and the 415 bp PstI fragments indicated in FIGS. 5 and 6. These clones produced no active IgG-binding protein, as indicated by colony immunoassay. The truncated protein produced by these clones would be expected to contain only a portion of the structure B1, and lack all amino acid sequences distal to B1.

Figure 6:
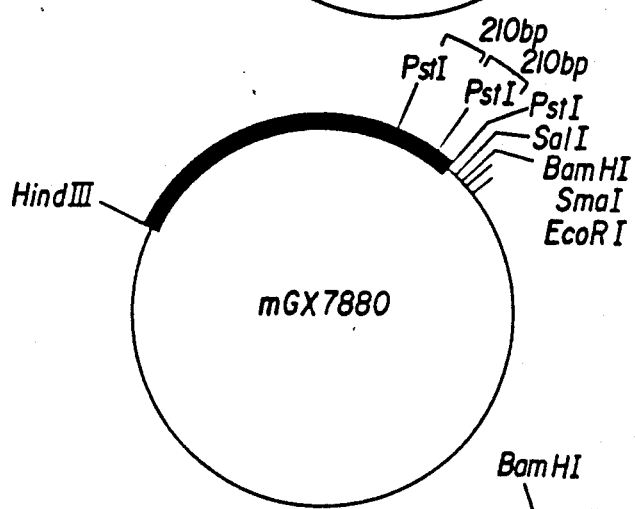
FIG. 6 shows the partial restriction map of mGX7880, a bacteriophage vector which contains two complete copies of the B structure and lacks all amino acid sequences distal to B1 and B2.

One of the clones obtained from the above transfection produced a positive result by colony immunoassay. Restriction analysis of RF DNA from this clone revealed that the phage DNA lacked the 415 bp PstI fragment, but retained the 210 bp fragment. Furthermore, the relative intensity of the 210 bp PstI fragment band on an ethidium bromide-stained agarose gel electrophoretogram suggested that the DNA carried two copies of the 210 bp fragment. DNA sequencing confirmed that the structure of this phage DNA (mGX7880) was as illustrated in FIG. 6. The protein encoded by the protein G gene carried on this phage DNA would be expected to contain two complete copies of the B structure, an intact B1 sequence followed by a chimera of B1 and B2. It would lack all amino acid sequences distal to B2. This structure results from the fact that the PstI sites which define the 210 bp fragment are located in the B repeating structures at positions corresponding to homologous sequences, and in the same relation to the reading frame of the protein. Polyacrylamide gel electrophoretic analysis revealed that *E. coli* bearing this DNA produced a protein with IgG-binding activity of approximately the expected size [Fahnestock, et al., *J. Bacteriol.* 1 67:870–880 (1986)].

These results indicate that the presence of the B repeated structure is a necessary and sufficient condition for IgG-binding activity of protein G. It was therefore concluded that the B repeating structure was the locus of IgG-binding activity in the molecule.

EXAMPLE IV

Expression of the Protein G Gene in Bacillus Subtilis

A synthetic oligonucleotide with a sequence resembling a transcription terminator was first inserted into mGX4547. The sequence of the oligonucleotide was:

```
5'-pTCGAAAAAAGAGACC-
  GGATATCCGGTCTCTTTTT-3'
```

It is self-complementary, and when double-stranded, produces single stranded ends with the same sequence as those produced by endonuclease SalI. To insert it into mGX4547, the phage DNA was digested with endonuclease SalI, phenol extracted and ethanol precipitated, then incubated with the synthetic oligonucleotide (which had been denatured by heating to 70° C. and slowly cooled to 23° C.) and DNA ligase under ligating conditions. Ligated DNA was used to transfect *E. coli* GX1210, and clones were screened for the loss of the SalI site and appearance of an EcoRV site, the recognition sequence for which is present on the synthetic oligonucleotide. One clone with the desired structure was designated mGX7872.

Next, sequences distal to the B2 repeated sequence were deleted from mGX7872. This was accomplished by oligonucleotide-directed in vitro mutagenesis. The following oligonucleotide was synthesized:

```
5'-pCGTTTTGAAGCGACCGGAACCTCT-
  GTAACC-3'.
```

This sequence is complementary on one half to sequences in mGX4547 immediately distal to the B2 sequence, and on the other half to sequences near those coding for the C-terminus of protein G. This oligonucleotide was used as a primer for the in vitro synthesis of double stranded RF DNA, with mGX4547 DNA as template, using standard methods. This DNA was used to transfect *E. coli* GX1210. Plaques were screened in situ for the ability of phage DNA they produced to hybridize to the radioactive oligonucleotide 5'-(32P)AGCGACC-GGAACCTC-3', which is complementary to the desired deleted sequence. One clone with the desired structure was identified and designated mGX7877. Its structure was verified by DNA sequence analysis. The deletion encompasses nucleotides 1651–1896 of the sequence shown in FIG. 3.

In order to allow fusion of the protein G coding sequence to an expression and secretion vector, a BamHI site was created in the sequence of mGX7877 by oligonucleotidedirected in vitro mutagenesis. A primer oligonucleotide, with the sequence,

```
5'-pGGTATCTTCGATTGGATCCGGTGAAT-
  CAACAGCGAATACCG-3',
``` was used to promote conversion of mGX7877 single stranded DNA to duplex DNA in vitro. This oligonucleotide was complementary to the sequence encoding protein G in mGX7877, but includes an additional 6 nucleotides, GGATCC, which comprise the recognition sequence for endonuclease BamHI, inserted near the beginning of the sequence encoding mature protein G (the product of removal of the secretion signal sequence). The resulting double stranded DNA was used to transfect *E. coli* GX1210. The RF DNA recovered from cells infected from plaques was screened for the presence of the BamHI site. One with the desired structure was designated mGX8402.

Figure 7:
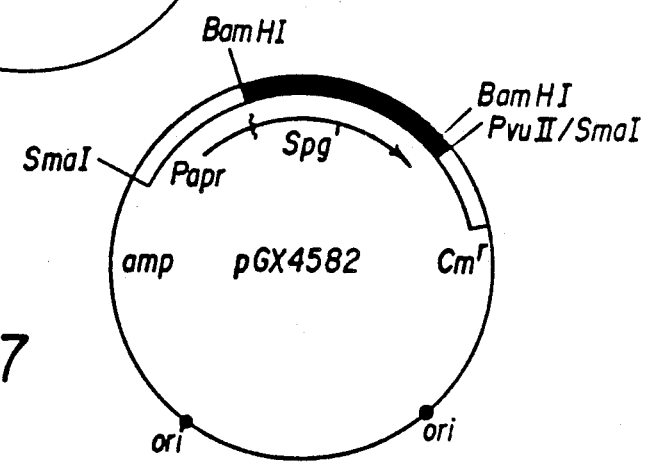
FIG. 7 shows a restriction map of plasmid pGX4582, a recombinant plasmid vector used to transform *B. subtilis* which contains a Protein G-encoding fragment.

A secretion vector containing the promoter and secretion signal sequence derived from a *Bacillus amyloliquefaciens* gene encoding subtilisin (apr) has been described by Vasantha and Thompson [*J. Bacteriol.* 165:837–842 (1984); and U.S. Pat. Application, Ser. No. 618,902, filed June 8, 1984, and the continuation-in-part thereof, Ser. No. 717,800, filed Mar. 29, 1985]. This vector, pGX2134, contains a BamHI site near the end of sequences encoding the secretion signal sequence, to which heterologous genes can be fused in order to promote their expression in *B. subtilis*, and the secretion of the protein product from the cell. In order to fuse protein G-encoding sequences to this vector, pGX2134 DNA was digested with endonucleases BamHI and PvuII. The RF DNA from mGX8402 was digested with endonucleases BsmHT and SmaI. After extraction with phenol and precipitation with ethanol, the digested DNA preparations were mixed and incubated with DNA ligase under ligation conditions, and the ligated DNA was used to transform *B. subtilis* GX8008 (apr deletion, npr deletion, spoOA677) protoplasts by standard methods. Transformants were selected for resistance to chloramphenicol and screened for production of protein G by colony immunoassay. A positive transformant was identified and designated GX8408 (pGX4582). The plasmid pGX4582 was shown to have the structure indicated in FIG. 7 by restriction analysis. It was presumably formed by insertion into pGX2134, between the BamHI and PvuII sites, of the BamHI fragment of mGX8402 bearing the protein G coding sequences, plus the small BamHI-SmaI fragment which is distal to the coding sequences in mGX8402.

Strain GX8408 was shown to produce a protein with the IgG-binding activity of protein G. This strain, where sequences distal to the B2 sequences are deleted, exhibited enhanced secretion of protein G-like material. After growth in appropriate media [Fahnestock and Fisher, *J. Bacteriol.* 165:796–804 1984], culture supernatants and cell-associated fractions were recovered and subjected to sodium dodecyl sulfate-polyacrylamide gel electrophoretic analysis. After electrophoretic separation, protein bands were transferred to nitrocellulose and stained immunochemically as described in Example I. Material with IgG-binding activity was found in both the culture supernatant and cell-associated fractions.

EXAMPLE V

Cloning the Gene Encoding Protein G From Streptococcus GX7805

Chromosomal DNA was isolated from a group G Streptococcus: clinical isolate designated GX7805 as described in Example I. A sample of the DNA was digested with restriction endonuclease HindIII and subjected to electrophoresis in a 1% agarose gel under standard conditions. The usefulness of HindIII for this purpose was indicated by restriction analysis of pGX4533 (Example I and FIG. 2) whereby it was determined that a DdIII site separated the protein G gene from adjacent downstream sequences which were shown to be responsible for preventing establishment of larger fragments on multicopy plasmids in *E. coli*. After electrophoresis, DNA fragments were transferred to nitrocellulose as described by Southern *J. Mol. Biol.* 98:503 1975. A band of approximately 2.4 kbp containing protein G-encoding sequences was located by hybridization with a radioactive probe consisting of the 1.9 kbp HindIII fragment indicated in FIG. 2, originally isolated from Streptococcus strain GX7809. The 1.9 kbp fragment probe was purified by agarose gel electrophoresis and eluted from the gel as described in Example I, then radioactively labeled with 32P by nick translation essentially as described by Rigby, et al. *J. Mol. Biol.* 113:237 (1977). Hybridization was carried out essentially as described by Wahl et al. [*Proc. Natl. Acad. Sci. USA* 76:3683–3687 (1979)]. After hybridization and washing to remove unhybridized probe, a radioactive band was located by autoradiography at a position corresponding to a length of 2.4 kbp.

A larger sample of the same GX7805 chromosomal DNA (6 ul) was digested with endonuclease HindIII, and the fragments were separated by electrophoresis in a 1% agarose gel (16 h at 0.35 volts/cm). After staining with ethidium bromide, portions of the gel containing bands of length 2–3 kbp (located relative to a standard consisting of endonuclease HindIII-digested bacteriophage lambda DNA) were excised and crushed to aid in the recovery of the DNA. The DNA was recovered after extraction with phenol as described in Example I.

Plasmid vector pGX1066 DNA (1 ug) was digested with endonuclease HindIII. Following extraction of the reaction mixture with phenol/chloroform/isoamyl alcohol (25:24:1), the DNA was precipitated by adding 0.1 volume 4M LiCl, 10 mM EDTA, 20 ug glycogen carrier, and 2.5 vol. 95% ethanol. 0.4 ug of the digested vector DNA was incubated with the recovered HindIII fragments of GX7805 DNA (90% of the material recovered from 6 ug chromosomal DNA) and T4 DNA ligase (International Biotechnologies, Inc., New Haven, CT), under ligation conditions as recommended by the manufacturer, in 20 ul, for 16 h at 15 C.

*E. coli* SK2267 cells were transformed with 15 ul of the ligated DNA as described in Example I, and the transformed cells were plated on colony immunoassay plates and assayed for the production of immunoglobulin-binding protein as described in Example I. A positive colony was identified. Plasmid DNA isolated from this transformant was found to consist of pGX1066 with a DNA insert of 2.4 kbp. An endonuclease HindIII fragment comprising the insert was subcloned in a bacteriophage M13mp9 vector. The DNA sequence of the 2.4 kbp HindIII fragment was determined, and is presented in FIG. 9.

EXAMPLE VI

Construction of Preferred Forms of the Protein G Gene for Secretion by *B. subtilis*

Preferred forms of Protein G are encoded by genes from which coding sequences upstream and downstream from the active B repeats (Example III) have been deleted. Such proteins, which exhibit the immunoglobulin binding activity of protein G, have enhanced stability toward proteolysis.

A. Deletion of upstream sequences

Figure 11:
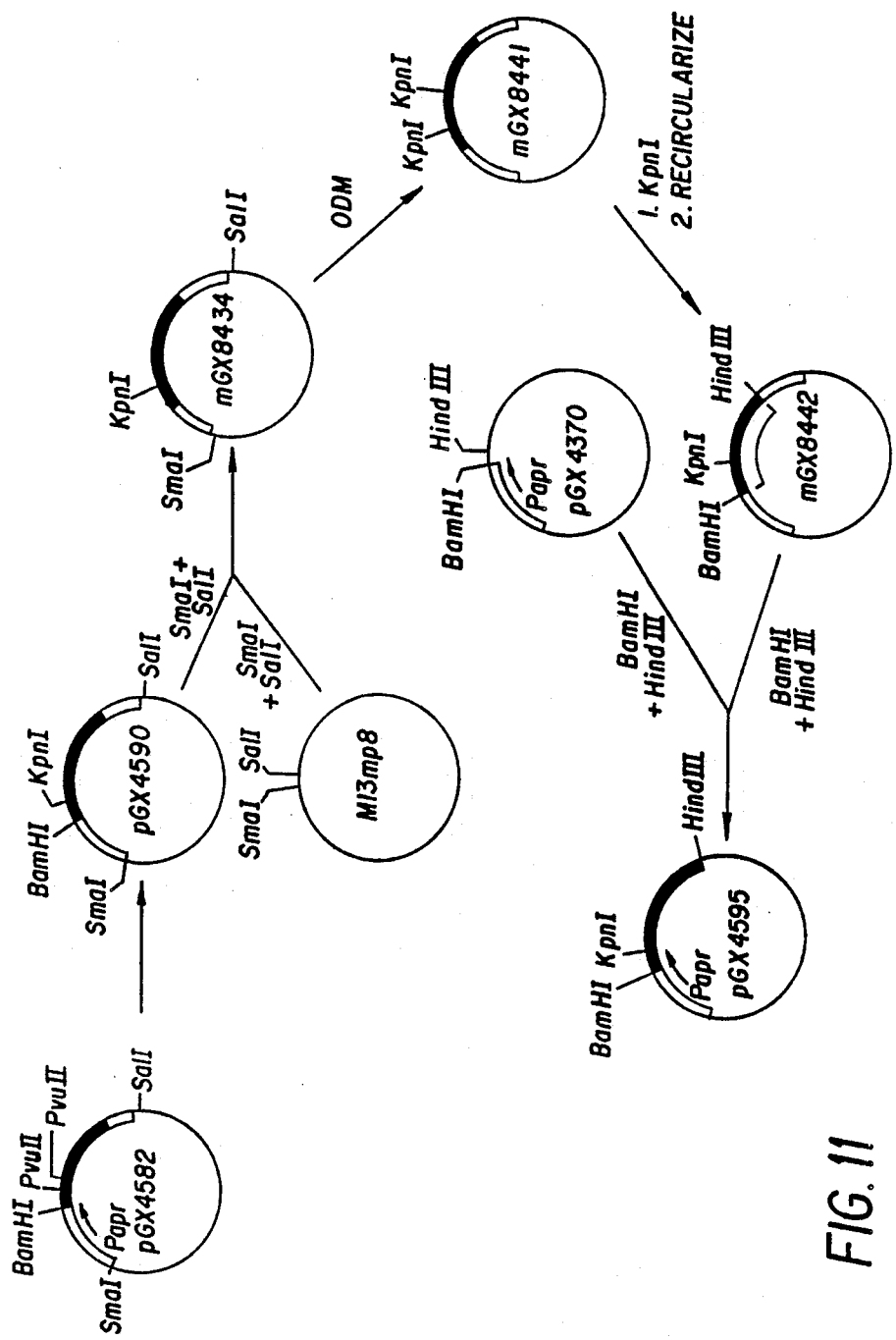
FIG. 11 depicts construction of plasmid pGX4595 from plasmid pGX4582 wherein coding sequences upstream from the active sites sequences have been deleted.

In order to accomplish the deletion of upstream sequences, plasmid pGX4582 (Example IV) was first modified to contain a unique cleavage site for restriction endonuclease KpnI (see FIG. 11). DNA of pGX4582 was digested with endonuclease PvuII, which cuts at two sites, both upstream from the A repeats. After phenol extraction and ethanol precipitation, the linear plasmid fragment was then recircularized in the presence of a 5'-phosphorylated selfcomplementary oligonucleotide with the sequence 5'-PCTGGGTACCCAG, which carries a recognition site for endonuclease KpnI, by treatment with T4 DNA ligase under ligation conditions. The ligated DNA was used to transform *E. coli* SK2267, and an ampicillin resistant transformant was isolated which contained a plasmid of the desired structure, which had acquired a unique KpnI site. This plasmid was designated pGX4590.

Next, the modified Protein G gene carried on pGX4590 was transferred to a bacteriophage M13 vector. DNA of pGX4590 was digested with endonucleases SmaI and SalI, which excise a fragment containing the entire Protein G encoding gene. Double stranded RF DNA of bacteriophage M13mp8 was also digested with SmaI and SalI, and both digested DNA preparations were extracted with phenol and precipitated with ethanol. The two preparations were then mixed and incubated with T4 DNA ligase under ligation conditions. The ligated DNA was used to transfect *E. coli* GX1210, and clones were screened for the presence of an insert fragment of the appropriate size. A clone containing the desired fragment was identified and designated mGX8434.

A second KpnI site was then created in the Protein G coding sequence carried on mGX8434, using the techniques of oligonucleotide-directed mutagenesis. An oligonucleotide was synthesized with the sequence

'-GTCAGTCTTAGGTAATGGGTACCCAGC-
TAAAATTTCATCTATCAG which is complementary to sequences carried on mGX8434 adjacent to those encoding domain B1, but carries a six-nucleotide insertion which comprises a recognition site for endonuclease KpnI. With single stranded DNA isolated from phage mGX8434 as template and the above defined oligonucleotide as primer, double stranded RF DNA was synthesized in vitro using standard methods. This DNA was used to transfect *E. coli* GX1210, and clones were screened for the presence of a second KpnI site. A clone with the desired structure was identified and designated mGX8441.

DNA of mGX8441 contains two KpnI sites, both created as described above, in such a manner that deletion of the sequences between them will create an in-frame fusion of sequences upstream from the first site and those downstream from the second. This deletion was accomplished by digesting RF DNA of mGX8441 with endonuclease KpnI, phenol-extracting and ethanol-precipitating the digested DNA, then recircularizing the larger RF fragment by incubating in dilute solution with T4 DNA ligase under ligation conditions. The ligated DNA was used to transfect *E. coli* GX1210, and clones were screened for loss of the small KpnI fragment. A clone with the desired structure was designated mGX8442. The structure of mGX8442 at the site of deletion was verified by DNA sequencing. It encodes a protein predicted to be the same as that encoded by pGX4582 from its N-terminus through amino acid residue Ala 38 of Protein G, followed by the sequence GlyTyrPro, encoded by the KpnI recognition sequence, then the sequence LeuProLysThrAsp (preceding domain B1) of pGX4582, and the remainder of the coding sequence of pGX4582.

In order to establish the coding sequence of mGX8442 in *B. subtilis*, the plasmid pGX4370 was used as a vector. This plasmid is similar to the plasmid pGX4312, which is described by P. Bryan et al. in U.S. Patent application No. 828,545 (filed Feb. 12, 1986), except that it contains additional sequences derived from a *B. amyloliquefaciens* subtilisinencoding gene. These sequences comprise a promoter, translation initiation sequences, and sequences encoding the secretion signal sequence, followed by a BamHI recognition sequence. They are derived from pGX2134, which is described in Example IV. The vector also carries replication origins active in both *B. subtilis* and *E. coli*, and markers which can be selected in both organisms (kanamycin resistance in *B. subtilis* and ampicillin resistance in *E. coli*). Plasmid pGX4370 DNA was digested with endonucleases BamHI and HindIII, phenol extracted and ethanol precipitated. Similarly, mGX8442 RF DNA was digested with endonucleases BamHI and HindIII, phenol extracted and ethanol precipitated. The digested DNA preparations were mixed and incubated with T4 DNA ligase under ligation conditions. The ligated DNA was used to transform *E. coli* SK2267, and an ampicillin resistant transformant with the desired structure was identified by restriction analysis and designated pGX4595. Plasmid pGX4595 DNA was then used to transform protoplasts of *B. subtilis* GX8008. A kanamycin resistant transformant, designated GX8446, was shown, by analysis similar to that outlined in Example IV above, to produce protein with the immunoglobulin binding activity of Protein G, and this protein could be detected in both the extracellular medium and the cell lysate fractions.

B. Deletion of Downstream Sequences

Figure 12:
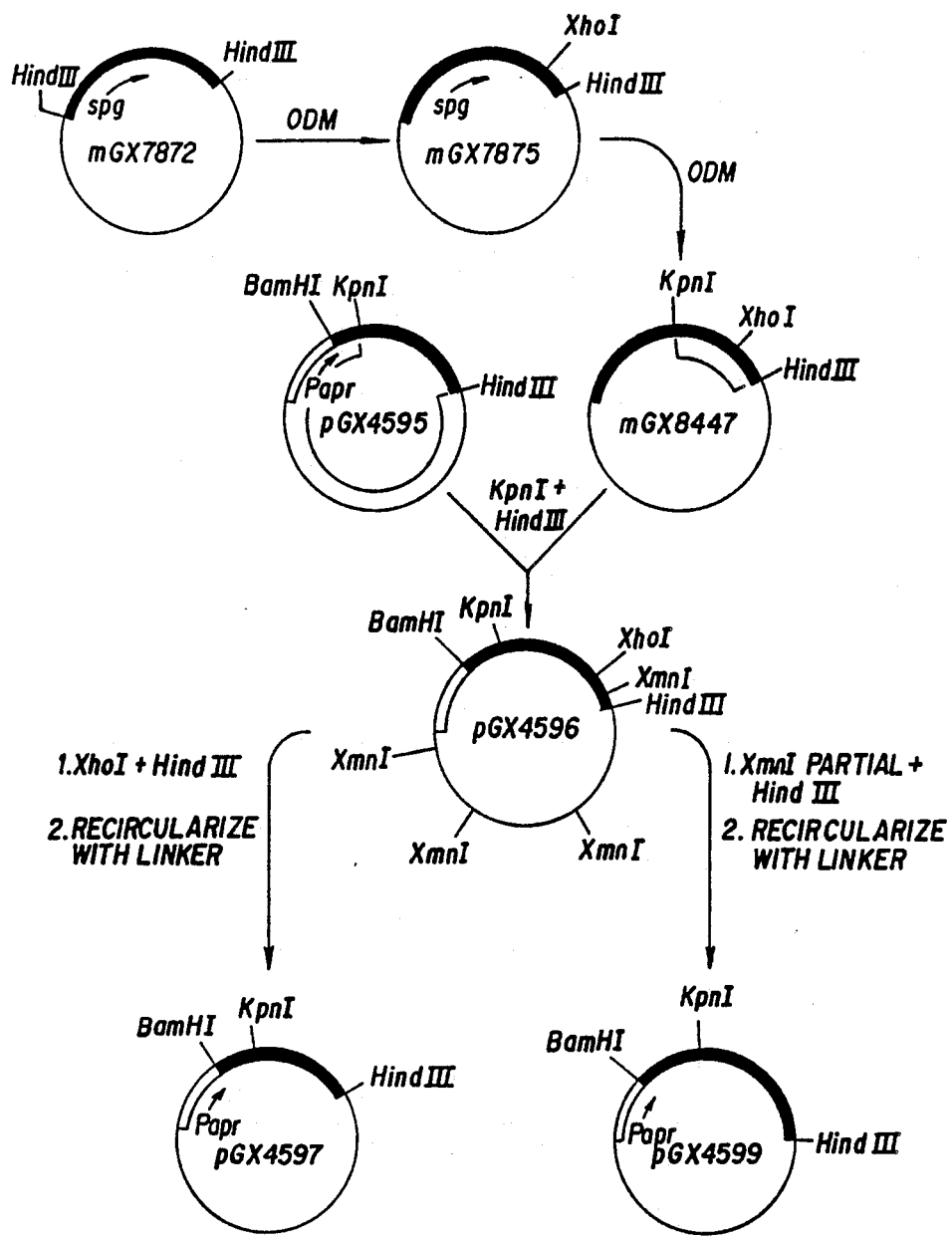
FIG. 12 depicts construction of plasmids pGX4597 and pGX4599 from plasmid mGX7872 wherein coding sequences downstream from the active sites have been deleted.

The starting point for constructions from which downstream sequences were variously deleted was a derivative of mGX7872 (Example IV) into which a site for endonuclease XhoI was inserted by oligonucleotide-directed mutagenesis following sequences encoding domain B2 (see FIG. 12). For this purpose, an oligonucleotide was synthesized with the sequence

5'-CAGTTGGTGCATCACCTCGAG-GAACCTCTGTAACC which is complementary to Protein G encoding sequences on mGX7872 immediately downstream from those encoding domain B2, but which contains a three-nucleotide insertion which creates an XhoI site. With single stranded DNA isolated from mGX7872 as template, and this oligonucleotide as primer, double stranded RF DNA was synthesized in vitro by standard methods, and used to transfect *E. coli* GX1210. Clones were screened for the presence of an XhoI site, and one with the desired structure was designated mGX7875. The altered sequence in mGX7875 was verified by DNA sequencing and shown to be as desired.

A KpnI site was then inserted into mGX7875 close to sequences encoding domain B1, at the position analogous to the second KpnI site inserted into mGX8434, which is described above. The same oligonucleotide, and methods analogous to those described above (for construction of mGX8441) were used. A clone with the desired structure was identified and designated mGX8447.

Downstream sequences derived from mGX8447 were then used to replace those present in pGX4595. For this purpose, RF DNA of mGX8447 and DNA of pGX4595 were separately digested with endonucleases KpnI and HindIII, phenol extracted and ethanol precipitated. The digested DNA preparations were mixed and incubated with T4 DNA ligase under ligation conditions. The ligated DNA was used to transform *E. coli* SK2267, and an ampicillin resistant transformant carrying a plasmid with the desired structure was identified by restriction analysis, and designated pGX4596. This plasmid is similar to pGX4595, except that sequences encoding the active portion of Protein G and downstream sequences (from the KpnI site preceding B1 to the HindIII site following the C-terminal coding sequences) are derived from mGX8447.

Plasmid pGX4596 was then used as starting point for various deletions involving downstream sequences. First, pGX4596 DNA was digested with endonuclease XhoI, which cuts at the site created by oligonucleotide-directed mutagenesis, described above, near the downstream end of sequences encoding domain B2, and HindIII, which cuts downstream from the end of the coding sequence. This digested DNA was subjected to preparative electrophoretic fractionation on a 0.7% agarose gel, and the larger of the two resulting fragments was eluted from the gel and recovered. A double stranded oligonucleotide adapter was constructed with the following structure:

5'P-TCGATCGTGCTAA
    AGCACGATTTCGA-5'P

The purified large XhoI-HindIII fragment derived from pGX4596 was recircularized in the presence of this adapter, the single stranded ends of which are complementary to the single stranded ends of the large fragment. This was accomplished by incubation of the fragment and adapter together in the presence of T4 DNA ligase under ligation conditions. The ligated DNA was used to transform *E. coli* SK2267, and an ampicillin resistant transformant carrying a plasmid with the desired structure was identified by screening for the presence of the endonuclease PvuI site which is present in the adapter sequence. This plasmid was designated pGX4597. It carries a truncated Protein G gene with the following designed structure . [B2]Met Val Thr Glu Val Pro Arg Ser Cys END
. . . ATGGTTACAGAGGTTCCTCGATCGTGCTAAAGCTT. . .

The C-terminal Cys residue encoded by the synthetic adapter in this construction is unique in the Protein G sequence encoded by this gene. One skilled in the relevant art will recognize that such a unique residue can provide a favorable site to which chemical reactions can be directed, such as those designed to immobilize the protein on a solid matrix or to attach various chemical functionalities or other proteins to it.

A second downstream deletion encompassed sequences downstream from repeat C5. This construction made use of an endonuclease XmnI site derived from the sequence at residue 1815 of the DNA sequence shown in FIG. 8. Plasmid pGX4596 contains a total of four XmnI sites. In order to obtain molecules cleaved only at the desired site in the Protein G coding sequence, pGX4596 DNA (5 micrograms per ml) was subjected to partial digestion with XmnI (100 units per ml) in the presence of ethidium bromide (40 micrograms per ml), for 60 min at 37° C. Under these conditions, digestion is mainly limited to a single cleavage, which results in a mixed population of linear molecules generated by cleavage at any one of the four sites. This digested DNA was extracted with phenol/chloroform-/isoamyl alcohol (25:24:1) and precipitated with ethanol, removing both the ethidium bromide and XmnI enzyme. The mixed linear DNA was then digested with HindIII. The HindIII site is located closer to the XmnI site in the Protein G coding sequence than to any of the other XmnI sites. The largest HindIII-XmnI fragment generated by digestion of the mixed XmnI linear population with HindIII is therefore derived from pGX4596 molecules which were cut only at the XmnI site in the Protein G coding sequence. This fragment was purified by preparative electrophoretic fractionation on a 0.7% agarose gel. The band with lowest mobility was excised, eluted from the gel, and recovered.

A double stranded oligonucleotide adapter was constructed with the structure

5'P-TGCCGGCTA
    ACGGCCGATTCGA-5'P

The single stranded end of this oligonucleotide is complementary to the single stranded end of the pGX4596 fragment, generated by HindIII cleavage. The purified fragment was recirculated in the presence of this adapter by incubation with T4 DNA ligase under ligation conditions. The ligated DNA was used to transform E. coli SK2267, and an ampicillin resistant transformant containing a plasmid with the desired structure was identified by restriction analysis. This plasmid was designated pGX4599. It carries a truncated Protein G gene with the following designed structure:

...[C5]Ala Glu Thr Ala Gly END
...GCTGAAACTGCCGGCTAAGCTT...

Plasmids pGX4597 and pGX4599 were used separately to transform protoplasts of B. subtilis GX8008. Kanamycin resistant transformants were selected and designated GX8455 (pGX4597) and GX8457 (pGX4599). Both strains were found to synthesize protein with the immunoglobulin binding activity of Protein G, and in both cases this protein was detected in both the extracellular medium and the cell lysate fractions.

EXAMPLE VII

Construction of Preferred Forms of the Protein G Gene for Expression in E. coli

Derivatives of the Protein G gene with various deletions were fused to a regulatable promoter system for advantageous expression in E. coli. The promoter used was a hybrid bacteriophage lambda promoter (OLPR) constructed by in vitro methods, and described by McKenney et al. in U.S. Pat. application No. 534,982 (filed Sept. 23, 1983). This promoter is carried on a plasmid pGX2606, which includes the translation initiation site of the phage lambda cro gene, with a BamHI site, situated as follows:

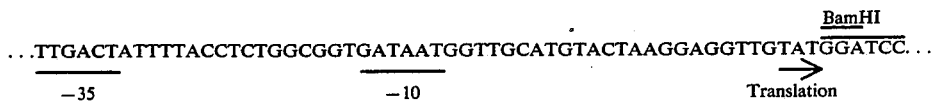

...TTGACTATTTTACCTCTGGCGGTGATAATGGTTGCATGTACTAAGGAGGTTGTATGGATCC...

−35        −10        Translation

In order to fuse modified Protein G genes derived from those carried on pGX4597 and pGX4599 at the BamHI site of the vector pGX2606, BamHI sites were created in pGX4597 and pGX4599, at the unique KpnI sites of those plasmids. For this purpose, a self-complementary oligonucleotide linker was synthesized with the following structure:

5'P-GGATCCGTAC
    CATGCCTAGG-5'P

The single stranded ends of this double stranded linker are complementary to the single stranded ends generated by digestion of the plasmids with endonuclease KpnI, and the linker incorporates a recognition site for endonuclease BamHI.

Figure 13:
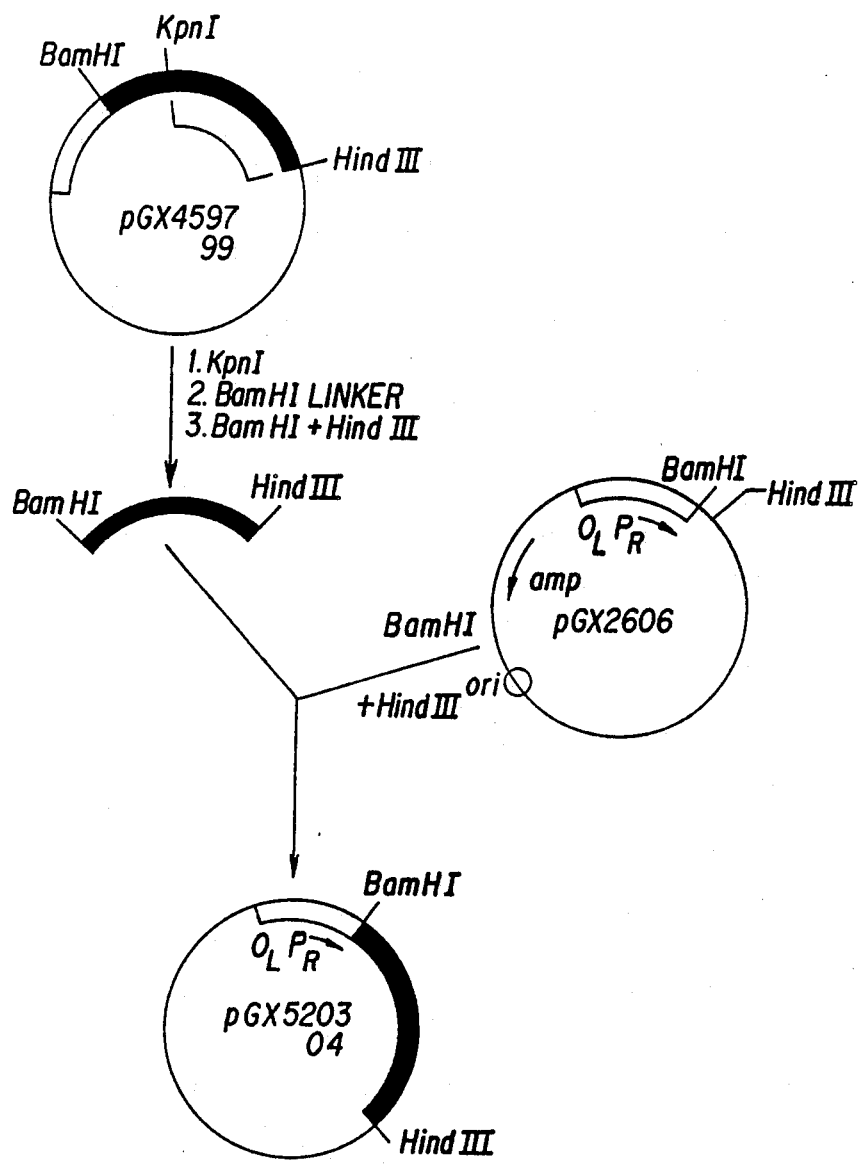
FIG. 13 depicts the construction of plasmids pGX5203 and pGX5204 from plasmids pGX4597 and pGX4599 respectively and the plasmid pGX2606 which contains the promoter OLPR.

DNA of plasmids pGX4597 and pGX4599 were separately digested with endonuclease KpnI, phenol extracted and ethanol precipitated (see FIG. 13). The digested DNA preparations were then incubated with the phosphorylated linker oligonucleotide and T4 DNA ligase under ligation conditions. DNA ligase was inactivated by incubation at 70° C. for 3 min, and the ligated DNA preparations were then digested with endonucleases BamHI and HindIII. Each digested DNA preparation was then subjected to preparative electrophoretic fractionation on a 1% agarose gel. The fragment of mobility corresponding to a length of between 400 and 700 bp was excised, extracted from the gel, and recovered. DNA of plasmid pGX2606 was digested with endonucleases BamHI and HindIII, and subjected to preparative electrophoresis on a 0.7% agarose gel to remove the small BamHI-HindIII fragment. The larger band was excised, eluted, and recovered.

The recovered pGX2606 fragment was mixed separately with the recovered pGX4597 and pGX4599 fragments, and incubated with T4 DNA ligase under ligation conditions. The ligated DNA preparations were used separately to transform E. coli GX1201 (nadA::TnlO delta 4(chlD-blu) (lambda cI857 delta BamHI)), a phage lambda lysogen carrying the cI857 gene encoding a thermolabile repressor protein. Transformants were selected at 30° C. for ampicillin resistance and screened by a variation of the immunoassay procedure described in Example I. Cells were grown at 30° C. on a cellulose acetate filter atop a nitrocellulose filter on a standard nutrient agar plate. After visible colonies had appeared, the plates were incubated at 42° C. for 4–6 hours, then the nitrocellulose filter was developed as described in Example I. A positive transformant identified in this way was found to contain plasmid of the desired structure by restriction analysis. The plasmid containing pGX4597-derived sequences was designated pGX5203, and the E. coli strain containing this plasmid was designated GX8464. The plasmid containing pGX4599-derived sequences was designated pGX5204, and the *E. coli* strain containing this plasmid was designated GX8465.

The designed structures of the modified Protein G genes carried by pGX5203 and pGX5204 are the same at the N-terminus:

```
         fMet Asp Tyr Pro Leu Pro Lys Thr Asp [ B1 ]...
...AAGGAGGTTGTATGGATCCGCCATTACCTAAGACTGACACTTAC...
```

The C-terminal sequences are the same as those of pGX4597 and pGX4599, respectively (Example VI).

Both GX8464 and GX8465 were shown to produce protein with the immunoglobulin binding activity of Protein G. In addition, both strains exhibited enhanced production and produced about 200 mg of recovered protein-G like material per liter of bacterial culture. Synthesis of this protein was found to be repressed at 30° C., and induced at 42° C., the mode of regulation expected of a gene under control of the hybrid phage lambda promoter OLPR in the presence of the thermolabile repressor encoded by the cI857 gene.

I claim:

1. A protein having the immunoglobulin binding specificity of protein G having the formula:

—(—B—b—)$_n$— wherein B is B1, B2, or B3, n is 1–20, B1is the immunoglobulin binding sequence;

```
THR TYR LYS LEU ILE LEU ASN GLY LYS THR
ACT TAC AAA TTA ATC CTT AAT GGT AAA ACA
   B1
                              LEU LYS
                              TTG AAA    1294
240
GLY GLU THR THR THR GLU ALA VAL ASP ALA
GGC GAA ACA ACT ACT GAA GCT GTT GAT GCT
   B1
                   250
                   ALA THR ALA
                   GCT ACT GCA    1333
           260
GLU LYS VAL PHE LYS GLN TYR ALA ASN ASP
GAA AAA GTC TTC AAA CAA TAC GCT AAC GAC
   B1
                         ASN GLY VAL
                         AAC GGT GTT    1372
        270
ASP GLY GLU TRP THR TYR ASP ASP ALA THR
GAC GGT GAA TGG ACT TAC GAC GAT GCG ACT
   B1
                              LYS THR PHE
                              AAG ACC TTT    1411
   280
THR VAL THR GLU
ACA GTT ACT GAA
   B1
```

B2 is the immunoglobulin binding sequence:

```
THR TYR LYS LEU VAL ILE ASN
ACT TAC AAA CTT GTT ATT AAT    1489
   B2
```

-continued
```
          310
GLY LYS THR LEU LYS GLY GLU THR THR THR
GGT AAA ACA TTG AAA GGC GAA ACA ACT ACT
                                      B2
                              LYS ALA VAL
                              AAA GCA GTA    1528
           320
ASP ALA GLU THR ALA GLU LYS ALA PHE LYS
GAC GCA GAA ACT GCA GAA AAA GCC TTC AAA
                                      B2
                         330
                         GLN TYR ALA
                         CAA TAC GCT    1567
             340
ASN ASP ASN GLY VAL ASP GLY VAL TRP THR
AAC GAC AAC GGT GTT GAT GGT GTT TGG ACT
                                      B2
                              TYR ASP ASP
                              TAT GAT GAT    1606
          350
ALA THR LYS THR PHE THR VAL THR GLU
GCG ACT AAG ACC TTT ACG GTA ACT GAA
                                 B2
```

B3 is a 55 amino acid hybrid sequence of B1 and B2, wherein the first N amino acids correspond to the first N amino acids of B1 or B2 and the last 55-N amino acids correspond to the last 55-N amino acids of B2 or B1, respectively; and b is the amino sequence:

```
                     290
LYS PRO GLU VAL ILE ASP ALA SER GLU
AAA CCA GAA GTG ATC GAT GCG TCT GAA    1450
   b
         LEU THR PRO ALA VAL THR
         TTA ACA CCA GCC GTG ACA
            b
``` with the proviso that the amino acid sequence of said protein is not the same as the amino acid sequence of wild type protein G or a fragment thereof.

2. The protein of claim 1, wherein said hybrid amino acid sequence B3 comprises the sequence:

```
Thr Tyr Lys Leu Val Ile Asn Gly Lys Thr
ACT TAC AAA CCT GTT ATT AAT GGT AAA ACA
                   B3

Leu Lys Gly Glu Thr Thr Thr
        TTG AAA GGC GAA ACA ACT ACT

Glu Ala Val Asp Ala Ala Thr Ala Glu Lys Val
GAA GCT GTT GAT GCT GCT ACT GCA GAA AAA GTC

Phe Lys Gln Tyr Ala Asn Asp Asn
        TTC AAA CAA TAC GCT AAC GAC AAC    1801

Gly Val Asp Gly Glu Trp Thr Tyr Asp Asp
GTT GTT GAC GGT GAA TGG ACT TAC GAC GAT
```

-continued

```
Ala  Thr  Lys  Thr  Phe  Thr  Val  Thr  Glu
GCG  ACT  AAG  ACC  TTT  ACA  GTT  ACT  GAA
            B3
```

3. A protein consisting essentially of one immunoglobulin binding site of protein G.

4. The protein of claim 3 consisting essentially of the immunoglobulin binding site $B_1$, wherein said binding site has the following amino acid sequence:

```
THR  TYR  LYS  LEU  ILE  LEU  ASN  GLY  LYS  THR
ACT  TAC  AAA  TTA  ATC  CTT  AAT  GGT  AAA  ACA
            B1
```

```
                              LEU  LYS
                              TTG  AAA   1294
```

```
240
GLY  GLU  THR  THR  THR  GLU  ALA  VAL  ASP  ALA
GGC  GAA  ACA  ACT  ACT  GAA  GCT  GTT  GAT  GCT
            B1
```

```
                   250
                   ALA  THR  ALA
                   GCT  ACT  GCA   1333
```

```
         260
GLU  LYS  VAL  PHE  LYS  GLN  TYR  ALA  ASN  ASP
GAA  AAA  GTC  TTC  AAA  CAA  TAC  GCT  AAC  GAC
            B1
```

```
                        ASN  GLY  VAL
                        AAC  GGT  GTT   1372
```

```
     270
ASP  GLY  GLU  TRP  THR  TYR  ASP  ASP  ALA  THR
GAC  GGT  GAA  TGG  ACT  TAC  GAC  GAT  GCG  ACT
            B1
```

```
                              LYS  THR  PHE
                              AAG  ACC  TTT   1411
```

```
280
THR  VAL  THR  GLU
ACA  GTT  ACT  GAA
     B1
```

5. The protein of claim 3 consisting essentially of the immunoglobulin binding site $B_2$, wherein said binding site has the following amino acid sequence:

```
THR  TYR  LYS  LEU  VAL  ILE  ASN
ACT  TAC  AAA  CTT  GTT  ATT  AAT   1489
            B2
```

```
         310
GLY  LYS  THR  LEU  LYS  GLY  GLU  THR  THR  THR
GGT  AAA  ACA  TTG  AAA  GGC  GAA  ACA  ACT  ACT
                              B2
```

```
                              LYS  ALA  VAL
                              AAA  GCA  GTA   1528
```

```
         320
ASP  ALA  GLU  THR  ALA  GLU  LYS  ALA  PHE  LYS
GAC  GCA  GAA  ACT  GCA  GAA  AAA  GCC  TTC  AAA
                              B2
```

```
                              330
                              GLN  TYR  ALA
                              CAA  TAC  GCT   1567
```

```
                   340
ASN  ASP  ASN  GLY  VAL  ASP  GLY  VAL  TRP  THR
AAC  GAC  AAC  GGT  GTT  GAT  GGT  GTT  TGG  ACT
                              B2
```

```
                              TYR  ASP  ASP
                              TAT  GAT  GAT   1606
```

```
                        350
ALA  THR  LYS  THR  PHE  THR  VAL  THR  GLU
GCG  ACT  AAG  ACC  TTT  ACG  GTA  ACT  GAA
            B2
```

6. The protein of claim 3 consisting essentially of the immunoglobulin binding site B3, wherein said binding site has the following amino acid sequence:

```
Thr  Tyr  Lys  Leu  Val  Ile  Asn  Gly  Lys  Thr
ACT  TAC  AAA  CCT  GTT  ATT  AAT  GGT  AAA  ACA
            B3
```

```
Leu  Lys  Gly  Glu  Thr  Thr  Thr
TTG  AAA  GGC  GAA  ACA  ACT  ACT
```

```
Glu  Ala  Val  Asp  Ala  Ala  Thr  Ala  Glu  Lys  Val
GAA  GCT  GTT  GAT  GCT  GCT  ACT  GCA  GAA  AAA  GTC
```

```
Phe  Lys  Gln  Tyr  Ala  Asn  Asp  Asn
TTC  AAA  CAA  TAC  GCT  AAC  GAC  AAC   1801
```

```
Gly  Val  Asp  Gly  Glu  Trp  Thr  Tyr  Asp  Asp
GTT  GTT  GAC  GGT  GAA  TGG  ACT  TAC  GAC  GAT
```

```
Ala  Thr  Lys  Thr  Phe  Thr  Val  Thr  Glu
GCG  ACT  AAG  ACC  TTT  ACA  GTT  ACT  GAA
            B3
```

* * * * *